US011564571B2

(12) United States Patent
Karsten et al.

(10) Patent No.: US 11,564,571 B2
(45) Date of Patent: Jan. 31, 2023

(54) SYSTEM AND METHOD FOR MAKING A RECOMMENDATION FOR A USER OF A LIFE MANAGEMENT SYSTEM

(71) Applicant: Zero360, Inc., Seattle, WA (US)

(72) Inventors: Peter Karsten, Windsor (GB); George Arriola, San Francisco, CA (US); Kouji Kodera, Mercer Island, WA (US)

(73) Assignee: ZERO360, INC., Seattle, WA (US)

(*) Notice: Subject to any disclaimer, the term of this patent is extended or adjusted under 35 U.S.C. 154(b) by 604 days.

(21) Appl. No.: 15/059,573

(22) Filed: Mar. 3, 2016

(65) Prior Publication Data
US 2017/0000348 A1 Jan. 5, 2017

Related U.S. Application Data

(63) Continuation of application No. PCT/GB2014/052692, filed on Sep. 4, 2014.
(Continued)

(30) Foreign Application Priority Data

Sep. 4, 2013 (GB) .................................. 1315764
Sep. 4, 2013 (GB) .................................. 1315765
Jan. 7, 2014 (GB) .................................. 1400225

(51) Int. Cl.
A61B 5/00 (2006.01)
G08B 6/00 (2006.01)
(Continued)

(52) U.S. Cl.
CPC .......... A61B 5/0022 (2013.01); A61B 5/0048 (2013.01); A61B 5/0205 (2013.01);
(Continued)

(58) Field of Classification Search
USPC ................................................ 705/7.11–7.42
See application file for complete search history.

(56) References Cited

U.S. PATENT DOCUMENTS 8,974,349 B2 * 3/2015 Weast ................... A61B 5/1118
482/8
11,094,413 B1 * 8/2021 Golenski ................ G16H 40/20
(Continued)

FOREIGN PATENT DOCUMENTS

WO WO 99/63498 12/1999
WO WO 2007/087298 8/2007
(Continued)

OTHER PUBLICATIONS

Official Action dated May 15, 2017 From the US Patent and Trademark Office Re. U.S. Appl. No. 15/059,636. (20 Pages).
(Continued)

Primary Examiner — Mustafa Iqbal
(74) Attorney, Agent, or Firm — Ziegler IP Law Group

(57) ABSTRACT

A life management system receives data from a client device worn by a user, the data comprising biotelemetry data and activity data collected about a user wearing the client device. The life management system generates snapshot information using information from a group consisting of: the biotelemetry data, activity data, social data associated with the user, and user profile information associated with the user. The life management system generates a recommendation using portions of the snapshot information, and updates the snapshot information with the recommendation. The life management system executes a recommendation associated with the snapshot information in accordance with the user controls associated with the user.

20 Claims, 16 Drawing Sheets

Related U.S. Application Data

(60) Provisional application No. 61/874,107, filed on Sep. 5, 2013, provisional application No. 61/874,219, filed on Sep. 5, 2013.

(51) Int. Cl.

| | | |
|---|---|---|
| G08B 7/00 | (2006.01) | |
| G08B 1/00 | (2006.01) | |
| G06Q 10/00 | (2012.01) | |
| G16H 40/00 | (2018.01) | |
| G16H 50/00 | (2018.01) | |
| G16H 15/00 | (2018.01) | |
| G16H 20/00 | (2018.01) | |
| G06F 3/00 | (2006.01) | |
| G08B 25/00 | (2006.01) | |
| G06F 1/00 | (2006.01) | |
| H04Q 9/00 | (2006.01) | |
| H04L 67/00 | (2022.01) | |
| A61B 5/0205 | (2006.01) | |
| G08B 7/06 | (2006.01) | |
| G08B 1/08 | (2006.01) | |
| G06Q 10/10 | (2012.01) | |
| G16H 40/63 | (2018.01) | |
| G16H 50/20 | (2018.01) | |
| G16H 40/20 | (2018.01) | |
| G16H 10/60 | (2018.01) | |
| G16H 20/30 | (2018.01) | |
| G16H 40/67 | (2018.01) | |
| A61B 5/369 | (2021.01) | |
| A61B 5/389 | (2021.01) | |
| G06F 3/01 | (2006.01) | |
| G06F 3/0484 | (2022.01) | |
| G08B 25/01 | (2006.01) | |
| G08B 25/10 | (2006.01) | |
| G06F 1/16 | (2006.01) | |
| G06F 3/0346 | (2013.01) | |
| G06F 3/04883 | (2022.01) | |
| A61B 5/024 | (2006.01) | |
| H04L 67/50 | (2022.01) | |
| H04L 67/306 | (2022.01) | |
| A61B 5/021 | (2006.01) | |
| A61B 5/0533 | (2021.01) | |

(52) U.S. Cl.
CPC .......... *A61B 5/02055* (2013.01); *A61B 5/369* (2021.01); *A61B 5/389* (2021.01); *A61B 5/681* (2013.01); *A61B 5/7445* (2013.01); *A61B 5/7475* (2013.01); *G06F 1/163* (2013.01); *G06F 3/015* (2013.01); *G06F 3/017* (2013.01); *G06F 3/0346* (2013.01); *G06F 3/0484* (2013.01); *G06F 3/04883* (2013.01); *G06Q 10/109* (2013.01); *G06Q 10/1093* (2013.01); *G06Q 10/1095* (2013.01); *G08B 1/08* (2013.01); *G08B 6/00* (2013.01); *G08B 7/06* (2013.01); *G08B 25/016* (2013.01); *G08B 25/10* (2013.01); *G16H 10/60* (2018.01); *G16H 15/00* (2018.01); *G16H 20/30* (2018.01); *G16H 40/20* (2018.01); *G16H 40/63* (2018.01); *G16H 40/67* (2018.01); *G16H 50/20* (2018.01); *H04Q 9/00* (2013.01); *A61B 5/021* (2013.01); *A61B 5/02438* (2013.01); *A61B 5/0533* (2013.01); *A61B 5/486* (2013.01); *A61B 5/4866* (2013.01); *A61B 5/4875* (2013.01); *G06F 2203/011* (2013.01); *G06F 2203/04808* (2013.01); *H04L 67/306* (2013.01); *H04L 67/535* (2022.05); *H04Q 2209/40* (2013.01)

(56) References Cited

U.S. PATENT DOCUMENTS

| | | | |
|---|---|---|---|
| 2007/0216537 A1* | 9/2007 | Park | G04C 21/34 340/691.1 |
| 2009/0002178 A1 | 1/2009 | Guday et al. | |
| 2009/0275354 A1* | 11/2009 | Bulmer | G06F 1/3203 455/522 |
| 2010/0125816 A1 | 5/2010 | Bezos | |
| 2011/0270836 A1* | 11/2011 | Yang | G06Q 10/06 707/737 |
| 2012/0062371 A1 | 3/2012 | Radiovojevic et al. | |
| 2012/0098764 A1 | 4/2012 | Asad et al. | |
| 2012/0194976 A1 | 8/2012 | Golko et al. | |
| 2012/0226779 A1 | 9/2012 | Crucs | |
| 2012/0277891 A1* | 11/2012 | Aragones | G06F 19/3481 700/91 |
| 2012/0283855 A1 | 11/2012 | Hoffman et al. | |
| 2012/0290950 A1 | 11/2012 | Rapaport et al. | |
| 2012/0316456 A1 | 12/2012 | Rahman et al. | |
| 2013/0007648 A1 | 1/2013 | Gamon et al. | |
| 2013/0161684 A1 | 6/2013 | Momma et al. | |
| 2013/0172691 A1 | 7/2013 | Tran | |
| 2013/0218982 A1 | 8/2013 | Hymel et al. | |
| 2013/0289419 A1 | 10/2013 | Berezhnyy et al. | |
| 2014/0065587 A1* | 3/2014 | Liebhart | G06F 19/3481 434/247 |
| 2015/0020081 A1* | 1/2015 | Cho | G06F 9/542 719/318 |
| 2015/0022438 A1 | 1/2015 | Hong | |
| 2015/0251074 A1* | 9/2015 | Ahmed | A61B 5/02405 700/91 |
| 2017/0003845 A1 | 1/2017 | Karsten et al. | |
| 2017/0004459 A1 | 1/2017 | Karsten et al. | |
| 2017/0031449 A1 | 2/2017 | Karsten et al. | |

FOREIGN PATENT DOCUMENTS

| | | |
|---|---|---|
| WO | WO 2012/095712 | 7/2012 |
| WO | WO 2013/088307 | 6/2013 |
| WO | WO 2015/033151 | 3/2015 |
| WO | WO 2015/033152 | 3/2015 |
| WO | WO 2015/033153 | 3/2015 |
| WO | WO 2015/035098 | 3/2015 |
| WO | WO 2015/063449 | 5/2015 |

OTHER PUBLICATIONS

International Search Report and the Written Opinion dated Mar. 9, 2015 From the International Searching Authority Re. Application No. PCT/GB2014/052692.

International Search Report and the Written Opinion dated Jul. 10, 2015 From the International Searching Authority Re. Application No. PCT/US2014/054159.

International Search Report and the Written Opinion dated Mar. 16, 2015 From the International Searching Authority Re. Application No. PCT/GB2014/052694.

International Search Report and the Written Opinion dated Feb. 26, 2015 From the International Searching Authority Re. Application No. PCT/GB2014/052690.

International Search Report and the Written Opinion dated Oct. 26, 2015 From the International Searching Authority Re. Application No. PCT/GB2014/052693.

Official Action dated Dec. 12, 2017 From the US Patent and Trademark Office Re. U.S. Appl. No. 15/059,636. (16 pages).

\* cited by examiner

SYSTEM AND METHOD FOR MAKING A RECOMMENDATION FOR A USER OF A LIFE MANAGEMENT SYSTEM

RELATED APPLICATIONS

This application is a Continuation of PCT Patent Application No. PCT/GB2014/052692 having International filing date of Sep. 4, 2014, which claims the benefit of priority of United Kingdom Patent Application Nos. 1400225.7 filed on Jan. 7, 2014, 1315764.9 filed on Sep. 4, 2013 and 1315765.6 filed on Sep. 4, 2013, and U.S. Provisional Patent Application Nos. 61/874,219 filed on Sep. 5, 2013 and 61/874,107 filed on Sep. 5, 2013. The contents of all of the above applications are incorporated by reference as if fully set forth herein.

FIELD AND BACKGROUND OF THE INVENTION

This invention relates to a life management system, and more specifically, to a life management system that makes recommendations for a user based on the user's real-time physical, social, and biotelometric activity.

In recent years, stress levels have been increasing for American adults, and many people report that they do not manage or reduce stress well. Stress can be caused by a difficulty to effectively multi-task with respect to activities such as work, exercise, nutritional intake, travel, and social engagements. Systems and methods for lowering stress and improving individuals' lifestyles are desirable.

Current health monitoring systems display a user's physical activity through sensors such as a pedometer, an elevation detector, or a heart rate monitor. However, these technologies are not necessarily used to lower an individual's stress level or make meaningful recommendations to the user regarding future activities or lifestyle choices. Further, these technologies are limited in the information that they can provide to a user, and do not provide an integrated life management solution allowing a user to better manage and improve multiple aspects of his lifestyle, including health, social, stress, schedule, organization, productivity, and overall well being. There does not currently exist a system that takes into account a user's physical activity, social activity, and biotelometric data to make recommendations to the user.

Additionally, health monitoring systems are generally user-centric, in the sense they do not allow third parties to analyze a user's physical activity, social activity, and biotelometric data to suggest and/or schedule actions that are beneficial to a user's health. Moreover, health monitoring systems lack means to coordinate third party services for their users and actively update calendars associated with their users based on the analyzed data.

SUMMARY OF THE INVENTION

Client devices associated with users of a life management system may collect data (e.g., biotelemetry data and/or activity data) about the user and provide it to a life management system. In certain embodiments, the life management system may perform certain actions based on the received data. Additionally, in some embodiments, the life management system may analyze the received data and/or make portions of the data accessible to an assistant associated with the user. The assistant may then perform certain actions and/or make recommendations based on the data. Additionally, in some embodiments, the life management system may utilize the received information to determined a mood of the user. The life management system, in accordance with the user's user controls, may then communicate the mood information to other users of the life management system. Additionally, in some embodiments, the user may configure user controls such that the life management system and/or the assistant may perform certain actions when one or more criteria are met.

According to one aspect of the present invention there is provided a method for making a recommendation for a user of a life management system, comprising: receiving user data relating to a user, the user data comprising biotelemetry data and activity data collected about a user wearing the client device; generating snapshot information using information from a group comprising: the biotelemetry data, activity data, social data associated with the user, and user profile information associated with the user; generating a recommendation using portions of the snapshot information; updating the snapshot information with the recommendation; and making a recommendation associated with the snapshot information in accordance with the user controls associated with the user.

Preferably, the biotelemetry data comprises information related to at least one of: heart rate, calories burned, blood pressure, skin temperature, brain activity, hydration level, galvanic skin response, a pedometer count, an optical skin and blood vessel dilation measurement, a blood glucose level, a blood oxygen level, a blood alcohol level, an electrocardiogram, an electroencephalogram, an electromyogram, a respiration rate, a measure of stress, a number of steps taken, a measure of calories used, a measure of activity, a movement from an accelerometer, a movement from a gyroscope, a response to mechanical or electrical stimuli, an environment temperature, an ambient ultraviolet light level, and an ambient $CO_2$ level.

Preferably, the activity data comprises information related to at least one of: steps taken, stairs climbed, exercise intensity, pace, sleep pattern, and sleep duration.

Preferably, the social data comprises information related to at least one of: a calendar for the user, an interest of the user, one or more connections to the user, and a location of the user.

Preferably, generating a recommendation using portions of the biotelemetry data and portions of the snapshot information, further comprises: determining values for one or more health parameters using portions of the snapshot information; and developing a recommendation based in part on a comparison between one or more of the values and corresponding threshold values.

Preferably, generating a recommendation using portions of the biotelemetry data and portions of the snapshot information, further comprises: analyzing a calendar associated with the user to identify a time slot for a recommended activity; and updating the recommendation with the time slot.

Preferably, generating a recommendation using portions of the snapshot information, further comprises: analyzing a calendar associated with the user and another calendar associated with a different user who is connected to the user, to identify a time slot for an activity; and updating the recommendation with the time slot.

Preferably, the recommendation comprises a nutritional recommendation, an exercise-related recommendation, a scheduling recommendation, a travel-related recommendation, a shopping recommendation (e.g., purchase a good and/or service), a sleeping recommendation, a suggestion to add a particular calendar entry an advertisement for a good, an advertisement for a service, a suggestion to improve one or more health parameters associated with the user, one or more advertisements that facilitate improving the one or more health parameters, one or more tips based on the user's activities (e.g., have a glass of water, take a break, etc.), or some combination thereof.

Preferably, the recommendation is based on at least one of an interest of the user, a schedule of the user, a location of the user, or health of the user.

Preferably the method further comprises: receiving a request from an assistant to the user for a portion of the snapshot information associated with the user; providing the portion of the snapshot information to the assistant in accordance with user controls associated with the user; and updating the snapshot information using actionable information received from the assistant.

Preferably, the assistant is a health coach, a personal assistant, or a customer service representative.

Preferably, the actionable information comprises: a new recommendation for the user, modifying the recommendation, adding a calendar entry to the user's calendar, purchasing a good, or purchasing a service.

Preferably, providing the portion of the snapshot information to the assistant in accordance with user controls associated with the user, comprises: providing a graphical user interface to the assistant that displays one or more health parameters, a momentum score for the user, analytical graphs for each of the displayed health parameters, and the recommendation.

Preferably, providing the portion of the snapshot information to the assistant in accordance with user controls associated with the user, comprises: providing a graphical user interface to the assistant that displays one or more calendar entries, one or more emails, and a momentum score for the user.

Preferably the method further comprises providing a graphical user interface to the user that displays information selected from the group consisting of: calendar information associated with the user, one or more health parameters associated with the user, analytical graphs for each of the displayed health parameters, the recommendation, and a momentum score.

Preferably, the method further comprises generating a card for presentation to the user, wherein the card includes the recommendation; and providing the card to the client device.

Preferably, the card also includes an icon related to a health parameter and the recommendation.

Preferably, generating a recommendation using portions of the snapshot information, further comprises: determining a value for a momentum score using portions of the snapshot information.

According to another aspect of the present invention, there is provided a method for making a recommendation for a user of a life management system, comprising: receiving user data relating to a user, the user data comprising biotelemetry data and activity data relating to the user; generating mood information using information from a group consisting of: the biotelemetry data, the activity data, social data associated with the user, and user profile information associated with the user; and providing, in accordance with user controls associated with the user, the mood information to a different user.

Preferably, the method further comprises designating a user a trusted user in accordance with user controls associated with the user, such that the trusted user may provide mood information to other users.

Preferably, the different user provides the mood information to the user.

According to yet another aspect of the present invention there is provided a method for making a recommendation for a user of a life management system, comprising: receiving one or more user controls associated with the user, that establish one or more criteria for performing an associated action; determining whether the one or more criteria have been met; responsive to the determination that the one or more criteria are met, automatically performing the action, the action including generating an entry within a calendar of the user, the entry reserving a time slot in the calendar associated with the action to be taken; and providing, for display, the entry to the user.

According to yet another aspect of the present invention there is provided a system for making a recommendation for a user of a life management system, comprising: receiving user data relating to user, the data comprising biotelemetry data and activity data collected about the; generating snapshot information using information from a group consisting of: the biotelemetry data, activity data, social data associated with the user, and user profile information associated with the user; generating a recommendation using portions of the snapshot information; updating the snapshot information with the recommendation; and making a recommendation associated with the snapshot information in accordance with the user controls associated with the user.

Preferably, the user data is received from a client device worn by the user, said client device being configured to collect biotelemetry data and activity data about the user.

Preferably, the biotelemetry data comprises information related to at least one of: heart rate, calories burned, blood pressure, skin temperature, brain activity, hydration level, galvanic skin response, a pedometer count, an optical skin and blood vessel dilation measurement, a blood glucose level, a blood oxygen level, a blood alcohol level, an electrocardiogram, an electroencephalogram, an electromyogram, a respiration rate, a measure of stress, a number of steps taken, a measure of calories used, a measure of activity, a movement from an accelerometer, a movement from a gyroscope, a response to mechanical or electrical stimuli, an environment temperature, an ambient ultraviolet light level, and an ambient $CO_2$ level.

Preferably, the activity data comprises information related to at least one of: steps taken, stairs climbed, exercise intensity, pace, sleep pattern, and sleep duration.

Preferably, the social data comprises information related to at least one of: a calendar for the user, an interest of the user, one or more connections to the user, and a location of the user.

Preferably, generating a recommendation using portions of the biotelemetry data and portions of the snapshot information, further comprises: determining values for one or more health parameters using portions of the snapshot information; and developing a recommendation based in part on a comparison between one or more of the values and corresponding threshold values.

Preferably, generating a recommendation using portions of the biotelemetry data and portions of the snapshot information, further comprises: analyzing a calendar associated with the user to identify a time slot for a recommended activity; and updating the recommendation with the time slot.

Preferably, generating a recommendation using portions the snapshot information, further comprises: analyzing a calendar associated with the user and another calendar associated with a different user who is connected to the user, to identify a time slot for an activity; and updating the recommendation with the time slot.

Preferably, the recommendation comprises a nutritional recommendation, an exercise-related recommendation, a scheduling recommendation, a travel-related recommendation, a shopping recommendation (e.g., purchase a good and/or service), a sleeping recommendation, a suggestion to add a particular calendar entry an advertisement for a good, an advertisement for a service, a suggestion to improve one or more health parameters associated with the user, one or more advertisements that facilitate improving the one or more health parameters, one or more tips based on the user's activities (e.g., have a glass of water, take a break, etc.), or some combination thereof.

Preferably, the recommendation is based on at least one of an interest of the user, a schedule of the user, a location of the user, or health of the user.

Preferably, the method further comprises receiving a request from an assistant, for a portion of the snapshot information associated with the user; providing the portion of the snapshot information to the assistant in accordance with user controls associated with the user; and updating the snapshot information using actionable information received from the assistant device.

Preferably, the request from an assistant is received from an assistant device associated with the assistant, and wherein the portion of the snapshot information is provided to the assistant device. Preferably, the assistant is a health coach, a personal assistant, or a customer service representative.

Preferably, the actionable information comprises: a new recommendation for the user, modifying the recommendation, adding a calendar entry to the user's calendar, purchasing a good, or purchasing a service.

Preferably, providing the portion of the snapshot information to the assistant device in accordance with user controls associated with the user, comprises: providing a graphical user interface to the assistant that displays one or more health parameters, a momentum score for the user, analytical graphs for each of the displayed health parameters, and the recommendation.

Preferably, providing the portion of the snapshot information to the assistant in accordance with user controls associated with the user, comprises: providing a graphical user interface to the assistant that displays one or more calendar entries, one or more emails, and a momentum score for the user.

Preferably, the method further comprises providing a graphical user interface to the user that displays information selected from the group consisting of: calendar information associated with the user, one or more health parameters associated with the user, analytical graphs for each of the displayed health parameters, the recommendation, and a momentum score.

Preferably, the method further comprises generating a card for presentation to the user, wherein the card includes the recommendation; and providing the card to the client device. Preferably, the card also includes an icon related to a health parameter and the recommendation. Preferably, generating a recommendation using portions of the snapshot information, further comprises: determining a value for a momentum score using portions of the snapshot information.

According to yet further aspect of the present invention there is provided a system for making a recommendation for a user of a life management system, comprising: receiving user data relating to a user, the data comprising biotelemetry data and activity data collected about a user; generating mood information using information from a group consisting of: the biotelemetry data, the activity data, social data associated with the user, and user profile information associated with the user; and providing, in accordance with user controls associated with the user, the mood information to a different user.

Preferably, the system further comprises: designating the user a trusted user in accordance with user controls associated with the user, such that the trusted user may provide mood information to other users. Preferably, the different user provides the mood information to the user.

Preferably, the user data is received from a client device worn by the user, the client device being configured to collect biotelemetry data and activity data.

According to yet further aspect of the present invention there is provided a system for making a recommendation for a user of a life management system, comprising: receiving one or more user controls, from the user, that establish one or more criteria for performing an associated action; determining whether the one or more criteria have been met; responsive to the determination that the one or more criteria are met, automatically performing the action, the action including generating an entry within a calendar of the user, the entry reserving a time slot in the calendar associated with the action to be taken; and providing, for display, the entry to the user.

Preferably, the one or more user controls are received from a client device associated with the user, and the generated entry is provided to the client device for display.

According to yet further aspect of the present invention there is provided a computer-implemented method comprising: receiving data from a client device worn by a user, the data comprising biotelemetry data and activity data collected about a user wearing the client device; generating snapshot information using information from a group consisting of: the biotelemetry data, activity data, social data associated with the user, and user profile information associated with the user; generating a recommendation using portions of the snapshot information; updating the snapshot information with the recommendation; and executing a recommendation associated with the snapshot information in accordance with the user controls associated with the user.

Preferably, the biotelemetry data comprises information related to at least one of: heart rate, calories burned, blood pressure, skin temperature, brain activity, hydration level, and galvanic skin response.

Preferably, the biotelemetry data comprises information related to at least one of: heart rate, calories burned, blood pressure, skin temperature, brain activity, hydration level, galvanic skin response, a pedometer count, an optical skin and blood vessel dilation measurement, a blood glucose level, a blood oxygen level, a blood alcohol level, an electrocardiogram, an electroencephalogram, an electromyogram, a respiration rate, a measure of stress, a number of steps taken, a measure of calories used, a measure of activity, a movement from an accelerometer, a movement from a gyroscope, a response to mechanical or electrical stimuli, an environment temperature, an ambient ultraviolet light level, and an ambient $CO_2$ level.

Preferably, the activity data comprises information related to at least one of: steps taken, stairs climbed, exercise intensity, pace, sleep pattern, and sleep duration.

Preferably, the social data comprises information related to at least one of: a calendar for the user, an interest of the user, one or more connections to the user in the life management system, and a location of the user.

Preferably, generating a recommendation using portions of the biotelemetry data and portions of the snapshot information, further comprises: determining values for one or more health parameters using portions of the snapshot information; and developing a recommendation based in part on a comparison between one or more of the values and corresponding threshold values.

Preferably, generating a recommendation using portions of the biotelemetry data and portions of the snapshot information, further comprises: analyzing a calendar associated with the user to identify a time slot for a recommended activity; and updating the recommendation with the time slot.

Preferably, generating a recommendation using portions the snapshot information, further comprises: analyzing a calendar associated with the user and another calendar associated with a different user of the life management system who is connected to the user, to identify a time slot for an activity; and updating the recommendation with the time slot.

Preferably, the recommendation comprises a nutritional recommendation, an exercise-related recommendation, a scheduling recommendation, a travel-related recommendation, a shopping recommendation (e.g., purchase a good and/or service), a sleeping recommendation, a suggestion to add a particular calendar entry an advertisement for a good, an advertisement for a service, a suggestion to improve one or more health parameters associated with the user, one or more advertisements that facilitate improving the one or more health parameters, one or more tips based on the user's activities (e.g., have a glass of water, take a break, etc.), or some combination thereof.

Preferably, the recommendation is based on at least one of an interest of the user, a schedule of the user, a location of the user, or health of the user.

Preferably the method further comprises: receiving a request from an assistant device, associated with an assistant, for a portion of the snapshot information associated with the user; providing the portion of the snapshot information to the assistant device in accordance with user controls associated with the user; and updating the snapshot information using actionable information received from the assistant device.

Preferably, the assistant is a health coach, a personal assistant, or a customer service representative.

Preferably, the actionable information comprises: a new recommendation for the user, modifying the recommendation, adding a calendar entry to the user's calendar, purchasing a good, or purchasing a service.

Preferably, providing the portion of the snapshot information to the assistant device in accordance with user controls associated with the user, comprises: providing a graphical user interface to the assistant that displays one or more health parameters, a momentum score for the user, analytical graphs for each of the displayed health parameters, and the recommendation.

Preferably, providing the portion of the snapshot information to the assistant device in accordance with user controls associated with the user, comprises: providing a graphical user interface to the assistant that displays one or more calendar entries, one or more emails, and a momentum score for the user.

Preferably the method further comprises: providing a graphical user interface to the user that displays information selected from the group consisting of: calendar information associated with the user, one or more health parameters associated with the user, analytical graphs for each of the displayed health parameters, the recommendation, and a momentum score.

Preferably the method further comprises: generating a card for presentation to the user, wherein the card includes the recommendation; and providing the card to the client device.

Preferably, the card also includes an icon related to a health parameter and the recommendation.

Preferably, generating a recommendation using portions of the snapshot information, further comprises: determining a value for a momentum score using portions of the snapshot information.

According to a yet further aspect of the present invention there is provided a computer-implemented method comprising: receiving data from a client device worn by a user in association with a life management system, the data comprising biotelemetry data and activity data collected about a user wearing the client device; generating mood information using information from a group consisting of: the biotelemetry data, the activity data, social data associated with the user, and user profile information associated with the user; and providing, in accordance with user controls associated with the user, the mood information to a different client device associated with another user of the life management system.

Preferably the method further comprises: designating a user of the life management system a trusted user in accordance with user controls associated with the user, such that the trusted user may provide mood information to other users of the life management system.

Preferably, a client device associated with the another user provides the mood information to the requesting client device.

According to a yet further aspect of the present invention there is provided a computer-implemented method comprising: receiving one or more user controls, from a user of a life management system via a client device associated with the user, that establish one or more criteria for performing an associated action; determining whether the one or more criteria have been met; responsive to the determination that the one or more criteria are met, automatically performing the action, the action including generating an entry within a calendar of the user, the entry reserving a time slot in the calendar associated with the action to be taken; and providing, for display, the entry to the client device associated with the user.

In one embodiment, data is received from a client device worn by a user, the data comprising biotelemetry data and activity data collected about a user wearing the client device. Snapshot information is generated using information from a group consisting of: the biotelemetry data, activity data, social data associated with the user, and user profile information associated with the user. A recommendation is generated using portions of the snapshot information, and the snapshot information is updated with the recommendation. The recommendation associated with the snapshot information is executed in accordance with the user controls associated with the user.

In another embodiment, data is received from a client device worn by a user in association with a life management system, the data comprising biotelemetry data and activity data collected about a user wearing the client device. Mood information is generated using information from a group consisting of: the biotelemetry data, the activity data, social data associated with the user, and user profile information associated with the user. The mood information is provided, in accordance with user controls associated with the user, to a different client device associated with another user of the life management system.

In yet another embodiment, one or more user controls are received from a user of a life management system via a client device associated with the user, that establish one or more criteria for performing an associated action. It is then determined whether the one or more criteria have been beet, and responsive to the determination that the one or more criteria are met, the action is automatically performed where the action includes generating an entry within a calendar of the user, and the entry reserves a time slot in the calendar associated with the action to be taken.

According to one aspect of the present invention there is provided a computer-implemented method comprising: receiving data from a client device worn by a user, the data comprising biotelemetry data and activity data collected about a user wearing the client device; generating snapshot information using information from a group consisting of: the biotelemetry data, activity data, social data associated with the user, and user profile information associated with the user; generating a recommendation using portions of the snapshot information; updating the snapshot information with the recommendation; and executing a recommendation associated with the snapshot information in accordance with the user controls associated with the user.

Preferably, the biotelemetry data comprises information related to at least one of: heart rate, calories burned, blood pressure, skin temperature, brain activity, hydration level, and galvanic skin response.

Preferably, the activity data comprises information related to at least one of: steps taken, stairs climbed, exercise intensity, pace, sleep pattern, and sleep duration.

Preferably, the social data comprises information related to at least one of: a calendar for the user, an interest of the user, one or more connections to the user in the life management system, and a location of the user.

Preferably, generating a recommendation using portions of the biotelemetry data and portions of the snapshot information, further comprises: determining values for one or more health parameters using portions of the snapshot information; and developing a recommendation based in part on a comparison between one or more of the values and corresponding threshold values.

Preferably, generating a recommendation using portions of the biotelemetry data and portions of the snapshot information, further comprises: analyzing a calendar associated with the user to identify a time slot for a recommended activity; and updating the recommendation with the time slot.

Preferably, generating a recommendation using portions the snapshot information, further comprises: analyzing a calendar associated with the user and another calendar associated with a different user of the life management system who is connected to the user, to identify a time slot for an activity; and updating the recommendation with the time slot.

Preferably, the recommendation comprises a nutritional recommendation, an exercise-related recommendation, a scheduling recommendation, a travel-related recommendation, a shopping recommendation (e.g., purchase a good and/or service), a sleeping recommendation, a suggestion to add a particular calendar entry an advertisement for a good, an advertisement for a service, a suggestion to improve one or more health parameters associated with the user, one or more advertisements that facilitate improving the one or more health parameters, one or more tips based on the user's activities (e.g., have a glass of water, take a break, etc.), or some combination thereof.

Preferably, the recommendation is based on at least one of an interest of the user, a schedule of the user, a location of the user, or health of the user.

Preferably, the method further comprises receiving a request from an assistant device, associated with an assistant, for a portion of the snapshot information associated with the user; providing the portion of the snapshot information to the assistant device in accordance with user controls associated with the user; and updating the snapshot information using actionable information received from the assistant device.

Preferably, wherein the assistant is a health coach, a personal assistant, or a customer service representative.

Preferably, the actionable information comprises: a new recommendation for the user, modifying the recommendation, adding a calendar entry to the user's calendar, purchasing a good, or purchasing a service.

Preferably, providing the portion of the snapshot information to the assistant device in accordance with user controls associated with the user, comprises: providing a graphical user interface to the assistant that displays one or more health parameters, a momentum score for the user, analytical graphs for each of the displayed health parameters, and the recommendation.

Preferably, providing the portion of the snapshot information to the assistant device in accordance with user controls associated with the user, comprises: providing a graphical user interface to the assistant that displays one or more calendar entries, one or more emails, and a momentum score for the user.

Preferably, the method further comprises providing a graphical user interface to the user that displays information selected from the group consisting of: calendar information associated with the user, one or more health parameters associated with the user, analytical graphs for each of the displayed health parameters, the recommendation, and a momentum score.

Preferably, the method further comprises generating a card for presentation to the user, wherein the card includes the recommendation; and providing the card to the client device.

Preferably, the card also includes an icon related to a health parameter and the recommendation.

Preferably, generating a recommendation using portions of the snapshot information, further comprises: determining a value for a momentum score using portions of the snapshot information.

According to another aspect of the present invention there is provided a computer-implemented method comprising: receiving data from a client device worn by a user in association with a life management system, the data comprising biotelemetry data and activity data collected about a user wearing the client device; generating mood information using information from a group consisting of: the biotelemetry data, the activity data, social data associated with the user, and user profile information associated with the user; and providing, in accordance with user controls associated with the user, the mood information to a different client device associated with another user of the life management system.

Preferably, the method further comprises a user of the life management system a trusted user in accordance with user controls associated with the user, such that the trusted user may provide mood information to other users of the life management system.

Preferably, wherein a client device associated with the another user provides the mood information to the requesting client device.

According to another aspect of the present invention there is provided a computer-implemented method comprising: receiving one or more user controls, from a user of a life management system via a client device associated with the user, that establish one or more criteria for performing an associated action; determining whether the one or more criteria have been met; responsive to the determination that the one or more criteria are met, automatically performing the action, the action including generating an entry within a calendar of the user, the entry reserving a time slot in the calendar associated with the action to be taken; and providing, for display, the entry to the client device associated with the user.

Further detail relating to various aspects of the present invention are described in the following patent applications, the contents of which are hereby incorporated by reference in their entirety:

United Kingdom Patent Application No. 1315765.6, titled "Processing system and method", filed Sep. 4, 2013;

United Kingdom Patent Application No. 1400225.7, titled "Processing system and method", filed Jan. 7, 2014;

United Kingdom Patent Application No. 1315764.9, titled "Device for providing alerts", filed Sep. 4, 2013;

U.S. Provisional Patent Application No. 61/874,107, titled "Intelligent Wristband and Life Management Environment," filed on Sep. 5, 2013;

U.S. Provisional Patent Application No. 61/874,219, titled "Life Management System", filed on Sep. 5, 2013; and four PCT applications filed on the same day as the present application by the same applicant titled "Processing system and method" (two applications with agent reference P41407WO and P41407WO-01), "Wearable device" (agent reference P43675WO), and "Device for providing alerts" (agent reference P41406WO) respectively.

Any feature in any of the abovementioned documents may be combined with any feature described herein in any appropriate combination.

The invention extends to any novel aspects or features described and/or illustrated herein. Further features of the invention are characterised by the other independent and dependent claims.

Any feature in one aspect of the invention may be applied to other aspects of the invention, in any appropriate combination. In particular, method aspects may be applied to apparatus aspects, and vice versa.

Furthermore, features implemented in hardware may be implemented in software, and vice versa. Any reference to software and hardware features herein should be construed accordingly.

Any apparatus feature as described herein may also be provided as a method feature, and vice versa.

As used herein, means plus function features may be expressed alternatively in terms of their corresponding structure, such as a suitably programmed processor and associated memory.

The invention also provides a computer program and a computer program product for carrying out any of the methods described herein and/or for embodying any of the apparatus features described herein, and a computer readable medium having stored thereon a program for carrying out any of the methods described herein and/or for embodying any of the apparatus features described herein.

The invention also provides a signal embodying a computer program for carrying out any of the methods described herein and/or for embodying any of the apparatus features described herein, a method of transmitting such a signal, and a computer product having an operating system which supports a computer program for carrying out any of the methods described herein and/or for embodying any of the apparatus features described herein.

It should also be appreciated that particular combinations of the various features described and defined in any aspects of the invention can be implemented and/or supplied and/or used independently.

The invention extends to methods and/or apparatus substantially as herein described with reference to the accompanying drawings.

BRIEF DESCRIPTION OF THE SEVERAL VIEWS OF THE DRAWINGS

The invention will now be described, purely by way of example, with reference to the accompanying drawings, in which.

DESCRIPTION OF SPECIFIC EMBODIMENTS
OF THE INVENTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures and may indicate similar or like functionality.

Figure 1:
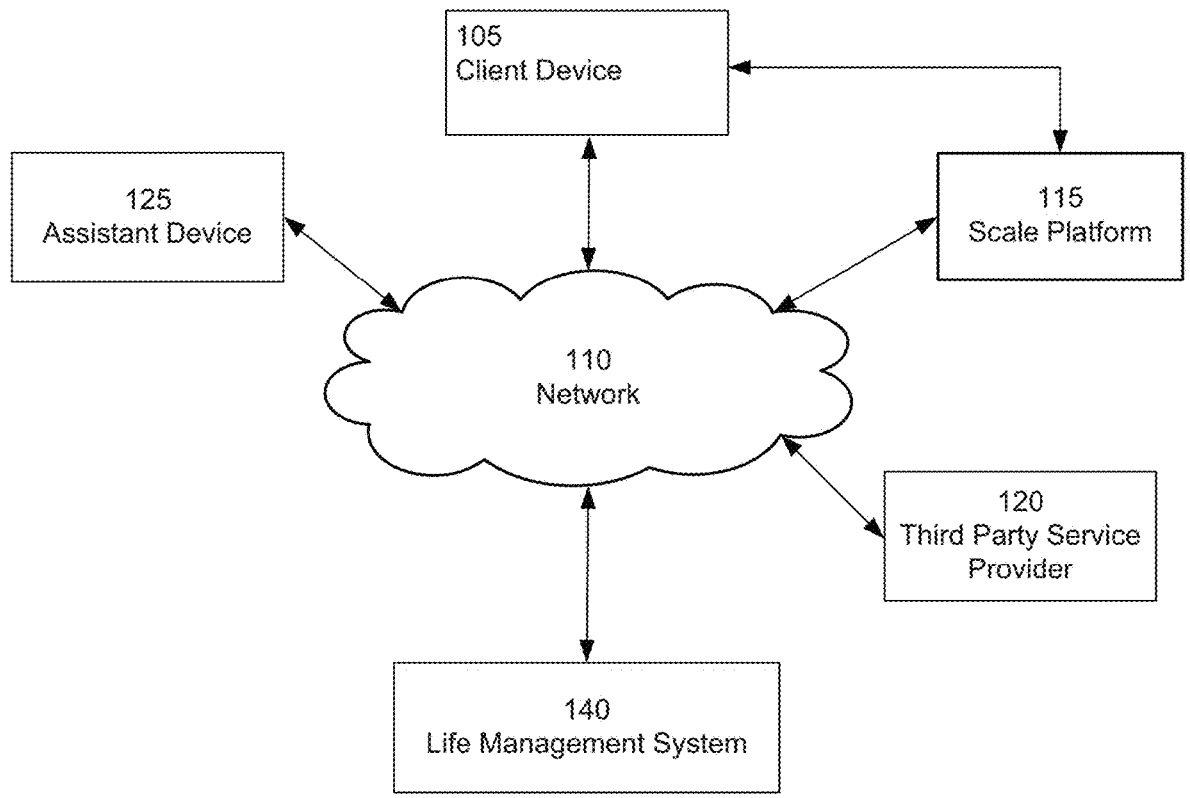
FIG. 1 is a high-level block diagram illustrating an embodiment of a life management environment including a life management system connected by a network to a client device, a scale platform, a third party service provider, and an assistant device.

FIG. 1 is a high-level block diagram illustrating an embodiment of a life management environment 100 including a life management system 140 connected by a network 110 to a client device 105, a scale platform 115, a third party service provider 120, and an assistant device 125. Here only one client device 105, scale platform 115, third party service provider 120, assistant device 125, and life management system 140 are illustrated but there may be multiple instances of each of these entities. For example, there may be thousands or millions of client devices 105 in communication with multiple life management systems 140.

The network 110 provides a communication infrastructure between the client device 105, the scale platform 115, the third party service provider 120, the assistant device 125, and the life management system 140. The network 110 is typically the Internet, but may be any network, including but not limited to a Local Area Network (LAN), a Metropolitan Area Network (MAN), a Wide Area Network (WAN), a mobile wired or wireless network, a private network, or a virtual private network. In one embodiment, the network 110 uses standard communications technologies and/or protocols. For example, the network 110 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 110 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 120 may be represented using any suitable format, such as hypertext markup language (HTML) or extensible markup language (XML). In some embodiments, all or some of the communication links of the network 110 may be encrypted using any suitable technique or techniques.

The scale platform 115 is a computing device that measures physical data associated with the user. Physical data is data that is indicative of the health of the user. Physical data may include, for example, body mass index, body fat percentage, heart rate, air quality measurement, or some combination thereof. In some embodiments, the scale platform 115 is a scale that when activated by the user (e.g., stood upon) measures the physical data associated with the user. The scale platform 115 communicates physical data to the client device 105 via the network 110, some wireless connection (e.g., WiFi, Bluetooth, etc.), or some combination thereof. Additionally, in some embodiments, the scale platform 115 may communicate physical data to, and receive software updates from the life management system 140 via the network 110.

The third party service provider 120 comprises one or more computer servers offering goods and/or services that the life management system 140 may offer to its users. Goods and/or services may include, for example, travel services, entertainment services, health services (e.g., gym membership), dining services, consumer goods, some other service, some other good, or some combination thereof. The services can be offered by a third party that is separate from the life management system 140 or, in some embodiments, can be offered by the life management system 140 itself.

The assistant device 125 is a computing device that allows an assistant to interact with snapshot information associated with one or more users of the life management system. An assistant is a third party that views snapshot information associated with a user of the life management system and recommends some action for the user based on the snapshot information. The assistant device 125 communicates the recommended action to the life management system 140. In some embodiments, an assistant may act as a health coach, concierge, personal assistant, well-being specialist, doctor, fitness trainer, dietitian, weight loss coach, sleep specialist, behavioral coach, habit coach, some other type of coach, or some combination thereof.

The client device 105 is a computing device that executes computer program modules which allow a user to interact with the life management system 140. The client device 105 is a computing device capable of receiving user input as well as transmitting and/or receiving data via the network 110. In one embodiment, a client device 105 is a conventional computer system, such as a desktop or laptop computer. Alternatively, a client device 105 may be a device having computer functionality, such as a personal digital assistant (PDA), a mobile telephone, a wearable computing device (e.g., GOOGLE® Glass, wristband, etc.) a smartphone or another suitable device. In one embodiment, the client device 105 is an intelligent wristband or other wearable device that collects data about the user wearing the device via sensors and provides an interface on which the user can interact with the wristband and the data.

A client device 105 is configured to communicate via the network 110. In one embodiment, a client device 110 executes an application allowing a user of the client device 105 to interact with the life management system 140, the third party service provider 120, or some combination thereof. For example, a client device 105 executes a browser application to enable interaction between the client device 105 and the life management system 140 via the network 110. In another embodiment, a client device 105 interacts with the life management system 140, the third party service provider 120, or both, through an application programming interface (API) running on a native operating system of the client device 105, such as IOS® or ANDROID™.

Additionally, in some embodiments, the client device 105 has biotelemetry monitoring capabilities, physical activity monitoring capabilities, or some combination thereof. For example, a wearable computing device (e.g., a wristband) provides biotelemetry data and/or activity data as further described in U.S. Provisional Patent Application No. 61/874,107, titled "Intelligent Wristband and Life Management Environment," filed on Sep. 5, 2013 and in a PCT application filed by the same applicant and on the same day as the present application titled "Intelligent Wristband and Life Management Environment", which are both hereby incorporated by reference in their entirety. In some embodiments, the biotelemetry monitoring capabilities may be provided via one or more peripheral devices (e.g., heart rate monitor) that are coupled to the client device 105. Biotelemetry data may include physical data, calories burned by the user, blood pressure of the user, skin temperature of the user, hydration level of the user, galvanic skin response of the user, brain activity of the user, sleep pattern of the user (e.g., duration and efficiency), or some combination thereof. In some embodiments, the client device 105 is configured to monitor biotelemetry data associated with the user (e.g., via one or more sensors on a wristband), and provide the biotelemetry data to the life management system 140. Activity data is data related to physical activities of the user. Activity data may include, for example, steps taken, stairs climbed, exercise intensity, pace, sleep pattern, sleep duration, some other activity, or some combination thereof. In some embodiments, the client device 105 has means for alerting the user, for example by delivering mild electric shocks to the user via at least one electrode and/or a vibration unit, as further described in United Kingdom application No. 1315764.9, titled "Device for providing alerts", filed Sep. 4, 2013 and PCT application filed by the same applicant and on the same day as the present application titled "Device for providing alerts" which are both hereby incorporated by reference in their entirety.

The client device 105 is configured to present snapshot information to the user. Snapshot information describes different and/or possible aspects of the life of the user. Snapshot information may include, e.g., biotelemetry data, activity data, user profile information, social data, one or more calendar cards, one or more health parameters (e.g., momentum level of the user, stress score, mood information, etc.), one or more recommendations, or some combination thereof. Additionally, the client device 105 is configured to enable the user to interact with the snapshot information, via, for example, a graphical user interface. Additionally, in some embodiments, the client device 105 is configured to present one or more cards to the user. A card presents portions of snapshot information (e.g., recommendations), advertisements, or some combination thereof, to a user of the client device 105. Additionally, in some embodiments, the client device 105 is configured to perform an action based on mood information received from the life management system 140. For example, the client device 105 may adjust colors associated with its display based on the mood information, or may change the display to include different types of information based on mood (e.g., a user who is stressed may receive a simplified display with less information, a user who is angry may receive a display that incorporates no items on the topic associated with his anger, a user who is sad may receive uplifting, brightly colored messages, and so forth).

The client device 105 is configured to communicate with the scale platform 115, the assistant device 125, the third party service provider 120, the life management system 140, or some combination thereof, via the network 110. Additionally, in some embodiments, the client device 105 is configured to receive physical data from the scale platform 115 via a wireless connection, e.g., WiFi, Bluetooth, etc. The client device 105 is configured to receive snapshot information, cards, advertisements, or some combination thereof, from the life management system 140.

Additionally, in some embodiments, the client device 105 is configured to send biotelemetry data and/or activity data, via the network 110, to the life management system 140. Additionally, in some embodiments, the client device 105 may send requests for one or more services from the third party service provider 120, via the network 110.

The life management system 140 generates snapshot information using social data associated with a user of the life management system 140, biotelemetry data associated with the user, user profile information associated with the user, activity data associated with the user, or some combination thereof. Social data describes activities and connections of the user. Social data may include, for example, a calendar associated with a user of the life management system, emails between the user and other users of the life management system 140, information from a social networking system associated with the user, connections between the user and other users of the life management system 140, or some combination thereof. In some embodiments, the life management system 140 is configured to provide some or all of the snapshot information to the client device 105.

In some embodiments, the life management system 140 provides some or all of the snapshot information associated with a user to the assistant device 125 of an assistant who is associated with the user. The life management system 140 is configured to receive one or more recommended actions from the assistant device 125. The life management system 140 is configured to adjust the snapshot information using the one or more recommended actions and provide some or all of the adjusted snapshot information to the client device 105. In some embodiments, all or a portion of the snapshot information is provided directly from the assistant device 125 to the client device 105 without or with limited involvement of the life management system 140.

As discussed in detail below, the life management system 140 is configured to interact with the third party service provider 120 to provide one or more services for users of the life management system 140. For example, the life management system 140 may select and provide one or more advertisements to the client device 105 based on targeting criteria of the advertisements and snapshot information associated with the user. Or in another example, the life management system 140 may interact with the third party service provider 120 to obtain a particular service and/or good for the user based on the snapshot information associated with the user (e.g., book a massage for the user when he is stressed).

In some embodiments, the life management system 140 is configured to calculate a mood of a user using some or all of the snapshot information associated with the user. The life management system 140 may then communicate mood information associated with one user to another user of the life management system 140. The other user, now aware of the mood of the user, may decide whether to interact with the user.

In some embodiments, the life management system 140 and/or other entities of the life management environment 100 may perform one or more of the functions described in Appendixes A-B.

Figure 2:
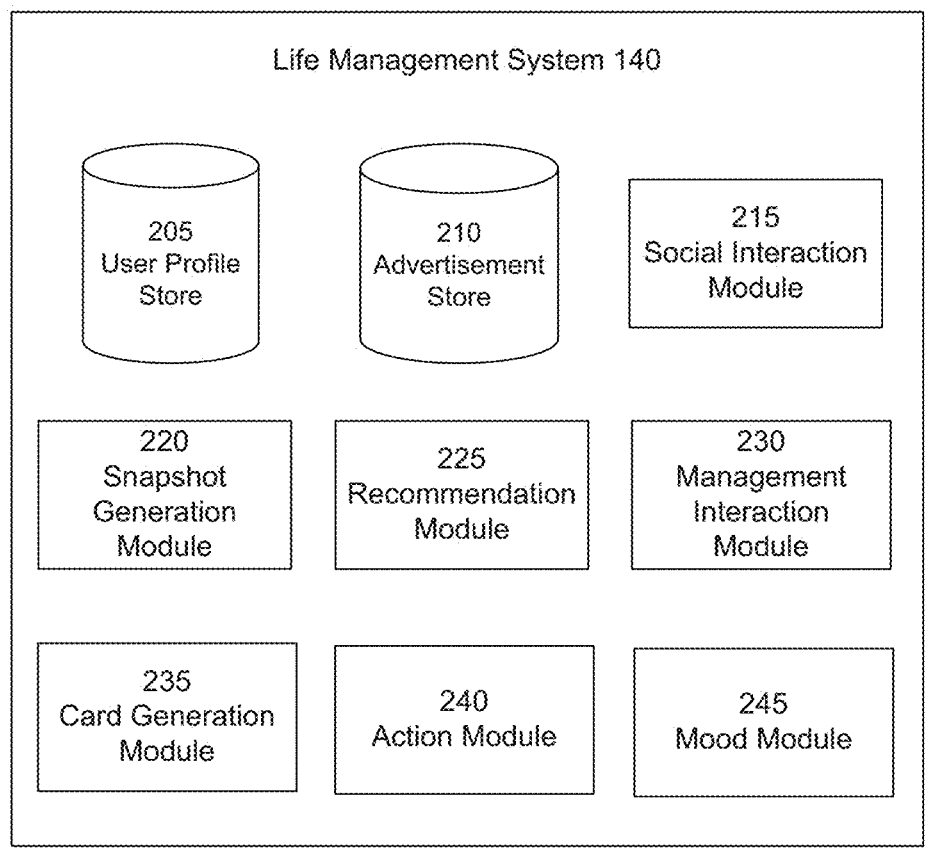
FIG. 2 is a high-level block diagram illustrating a detailed view of the life management system according to one embodiment.

FIG. 2 is a high-level block diagram illustrating a detailed view of the life management system 140 according to one embodiment. The life management system 140 is comprised of modules including a user profile store 205, an advertisement store 210, a social interaction module 215, a snapshot generation module 220, a recommendation module 225, a management interaction module 230, a card generation module 235, an action module 240, and a mood module 245. Some embodiments of the life management system 140 have different modules than those described here. Similarly, the functions can be distributed among the modules in a different manner than is described here.

Each user of the life management system 140 is associated with a user profile, which is stored in the user profile store 205. Information stored in the user profile is known as user profile information. A user profile includes declarative information about the user that was explicitly shared by the user and may also include profile information inferred by the life management system 140. Examples of information stored in a user profile include login and password information, biographic, demographic, and other types of descriptive information, type of employment, health descriptors (e.g., diet, exercise level, smoker/nonsmoker, medication allergies, etc.), educational history, gender, location, or other medical information associated with the user, user controls, or some combination thereof.

User controls control how some or all of snapshot information (e.g., mood information, user profile information, biotelemetry data, activity data, recommendations, etc.) associated with the user may be used by the life management environment 100. In some embodiments, user controls are used to set authorization levels for assistants and/or the action module 240. An authorization level determines whether the associated entity (e.g., assistant and/or life management system 140) is able to perform an action without first getting express approval from the user. Authorization levels may be set to a high level, such that an entity must obtain express approval from a user to perform an action (e.g., purchase a good/service, add a calendar entry, etc.), or be set to a low level, such that an entity may perform an action without first getting express approval from the user.

Additionally, different entities may have different authorization levels, and the same entity may have different authorization levels depending on the type of action involved.

Additionally, in some embodiments, authorization levels for entities may be customized based on the type of action and one or more criteria selected by the user. Criteria may include, for example, identity of the requesting entity, identity of some other entity, time span, size of a good, model of a good, price range of a good/service, brand of a good/service, price of a good/service, travel destination, preferred mode of transportation (e.g., airline, train, car, etc.), preferred transportation carrier, preferred merchant, preferred method of payment, preferred good/service, geographic location, portions of a user's biotelemetry data, portions of a user's activity data, portions of a user's physical data, portions of a user's social data, portions of a user's user profile information, or some combination thereof. For example, a user may configure the user controls such that an entity generally has a low authorization level, but if one or more particular criteria are met, the entity's authorization level is high.

Additionally, in some embodiments, the user controls may be configured to enable the action module 240 to perform certain actions when one or more criteria are met. User controls may define one or more actions that may be performed if the one or more criteria are met. The actions may be performed automatically, manually, or automatically and subject to additional conditions. An action may include, for example, purchase of a good, purchase of a service, adding a calendar entry, modifying a calendar entry, deleting a calendar entry, shifting tasks between entities in the life management environment 100, shifting data between entities in the life management environment 100, using conditions in one part of the life management environment 100 to set conditions in another part of the life management environment 100, automatically performing one or more actions in accordance with a user's user controls, or some combination thereof. The user controls may be configured such that the user selects an action before or after identifying one or more criteria associated with the action.

The advertisements store 210 stores one or more advertisement requests for goods and/or services. The advertisement store 210 receives one or more advertisements requests from the third party service provider 125, some other advertiser, an ad exchange, or some combination thereof. An advertisement request includes advertisement content and a bid amount. The advertisement content is text, image, audio, video, or any other suitable data presented to a user. In various embodiments, the advertisement content also includes a landing page specifying a network address to which a user is directed when the advertisement is accessed. The bid amount is associated with an advertisement by an advertiser and is used to determine an expected value, such as monetary compensation, provided by an advertiser (e.g., the third party service provider 125) to the life management system 140 if the advertisement is presented to a user, if the advertisement receives a user interaction, or based on any other suitable condition. For example, the bid amount specifies a monetary amount that the life management system 140 receives from the advertiser if the advertisement is displayed and the expected value is determined by multiplying the bid amount by a probability of the advertisement being accessed by a user.

Additionally, an advertisement request may include one or more targeting criteria specified by the advertiser. Targeting criteria included in an advertisement request specifies one or more characteristics of users eligible to be presented with advertisement content in the ad request. For example, targeting criteria are used to identify users having snapshot information satisfying at least one of the targeting criteria.

The social interaction module 215 maintains social data associated with users of the life management system 140. The social interaction module 215 is able to interact with, in accordance with a user's user controls, a user's email (external and/or internal to the life management system 140), calendar (external and/or internal to the life management system 140), connections in the life management system 140, connections to an external social networking system, or some combination thereof. The social interaction module 215 generates social data using information collected from users' calendars internal to the life management system 140, calendars external to the life management system 140, likes and/or dislikes within the life management system 140, likes and/or dislikes on external social networking systems, received emails (external/and or internal to the life management system 140), geo-location of client devices 105, or some combination thereof.

The social interaction module 215 interacts with calendars associated with users of the life management system 140. Each calendar includes one or more calendar entries. The social interaction module 215 may update (i.e., create, delete, or modify) calendar entries associated with one or more calendars based on instructions from the client device 105 associated with the user, the management interaction module 220, the action module 240, or some combination thereof. A calendar entry is associated with one or more information fields. An information field may include various information items associated with the entry, e.g., date, time period, name, description, reminder information (e.g., alert user 30 minutes prior to event), location information (e.g., address and/or map), attendee information (names and/or profile pictures of parties to the event), mood information for one or more participants (e.g., before, during, and/or after event), document attachments, biotelemetry data associated with one or more users associated with a calendar entry, or some combination thereof. In some embodiments, the social interaction module 215 may send notifications to participants associated with calendar entries. Further detail relating to calendar aspects are described in United Kingdom Patent Application No. 1400225.7, titled "Processing system and method", filed Jan. 7, 2014 and a PCT application filed by the same applicant on the same day as the present application titled "Processing system and method". Both of these documents are hereby incorporated by reference in their entirety.

The snapshot generation module 220 generates snapshot information associated with one or more users of the life management system 215. In some embodiments, the snapshot generation module 220 generates one or more health parameters for a user based in part on some, or all of, the social data associated with the user, the biotelemetry data associated with the user, the activity data associated with the user, user profile information associated with the user, or some combination thereof. In some embodiments, a health score represents a sleep efficiency of the user, a stress level of the user, an exercise intensity of the user, a general activity level of the user, a self-control or motivational level of the user, blood pressure of the user, obesity of the user, a momentum level of the user, mood information of the user, or some combination thereof. For example, a stress level score of the wearing user may be determined by combining at least a portion of the social data (e.g., schedule) and biotelemetry data (e.g., heart rate) of the wearing user. In another example, an exercise intensity score of the wearing user may be determined by combining by analyzing portions of the biotelemetry data (e.g., heart rate) and activity data (e.g., pace). The momentum level of the user describes the overall well being of the user. In some embodiments, the momentum score may be generated based a user's performance relating to assigned goals. For example, an assistant may assign certain tasks (e.g., run two miles weekly) to the user. The snapshot generation module 220 may determine a momentum level associated with the user based on the user's performance of the assigned tasks. Additionally, in some embodiments, the momentum score may be further increased if the user goes above and beyond the assigned tasks (e.g., running 4 miles weekly). Additionally, in some embodiments, the momentum level may take into account the performance of other users who were assigned the same task. In this manner, the momentum score may take into account the relative differences between the user's performance and other users of the life management system 140.

Mood information of a user is an estimation of the emotional state of the user based on an analysis of the social data associated with the user, biotelemetry data associated with the user, activity data associated with the user, user profile information associated with the user, or some combination thereof. Mood information may indicate, for example, a user is excited, happy, sad, fatigued, angry, grumpy, or any other emotional state capable of being inferred by the snapshot generation module 220. For example, mood information may be determined from a user's hear rate and galvanic skin response. In some embodiments, mood information may be determined via manual entry of by the user of the user's mood. In some embodiments, the mood information may include a numerical score.

Additionally, in some embodiments, the snapshot generation module 220 may prompt a user to identify their current mood. In some embodiments, the snapshot generation module 220 may perform a machine learning algorithm using the received feedback, social data associated with the user, biotelemetry data associated with the user, activity data associated with the user, user profile information associated with the user, or some combination thereof. For example, social data, biotelemetry data, activity data, user profile information, feedback, or some combination thereof, can be considered input signals that are analyzed by the machine learning algorithm. The machine learning algorithm can be trained on a set of signals associated with users of known moods that correspond to particular data taken from the social data, the biotelemetry data, the activity data, the user profile information, or some combination thereof. Once the machine learning algorithm has been trained on a known data set, the algorithm can be used for determining mood information based on a user's social data, biotelemetry data, activity data, user profile information, or some combination thereof. Further detail relating to 'mood' aspects are described in United Kingdom Patent Application No. 1400225.7, titled "Processing system and method", filed Jan. 7, 2014 and a PCT application filed by the same applicant on the same day as the present application titled "Processing system and method". Both of these documents are hereby incorporated by reference in their entirety.

The recommendation module 225 generates one or more recommendations for users of the life management system 140 using the generated snapshot information, advertisement requests, or some combination thereof. A recommendation is a suggestion to the user to perform some action.

A recommendation may include, for example, a nutritional recommendation, an exercise-related recommendation, a scheduling recommendation, a travel-related recommendation, a shopping recommendation (e.g., purchase a good and/or service), a sleeping recommendation, a suggestion to add a particular calendar entry an advertisement for a good, an advertisement for a service, a suggestion to improve one or more health parameters associated with the user, one or more advertisements that facilitate improving the one or more health parameters, one or more tips based on the user's activities (e.g., have a glass of water, take a break, etc.), or some combination thereof. The recommendation module 225 is configured to update the snapshot information with the one or more generated recommendations.

In some embodiments, the recommendation module 225 analyzes some or all of the generated snapshot information to develop recommendations to improve one or more health parameters associated with the user. In some embodiments, the one or more health parameters (e.g., sleep efficiency, a stress level, an exercise intensity, etc.) have corresponding activities of a particular category that when performed by a user generally have a beneficial effect on the corresponding health parameter. For example, a stress level score may have certain corresponding stress reduction activities (e.g., exercise, diet, increased sleep, etc.). In some embodiments, the recommendation module 225 determines whether one or more health parameters for users of the life management system 140 are below a threshold value. The recommendation module 225 may automatically calculate the threshold values, receive the threshold values from the user, receive threshold values from an assistant associated with the user, or some combination thereof. If a health score is below the threshold value, the recommendation module 225 may recommend one or more corresponding activities (e.g., stress reduction activities to reduce stress of the user). The recommendation module 225 may analyze the social data of the user to suggest time slots available to perform the one or more recommended activities.

In some embodiments, the recommendation module 225 may identify one or more advertisements in the advertisement store 210 that are associated with the one or more recommended activities. The recommendation module 225 may analyze the advertisement content, advertisement targeting criteria, user snapshot information, or some combination thereof, to determine what effect the service/product advertised may have on one or more health parameters of the user. The recommendation module 225 may then generate one or more recommendations using the appropriate advertisements. For example, a recommendation to reduce the stress level of the user may be generated that includes an advertisement for a massage.

Additionally, in some embodiments, the recommendation module 225 may analyze snapshot information associated with users of the life management system 140 that are connected to the user, in accordance with the users' user controls, to generate one or more recommendations for the user and the user's connections. For example, the recommendation module 225 may determine that both the user and a connection of the user need to get more exercise, and that they are both free Saturday afternoon. The recommendation module 225 may generate a recommendation for both the user and the connection to the user to participate in the same spin class occurring on Saturday at 2:00 pm.

Additionally, in some embodiments, the recommendation module 225 may take into account the geographic locations of the user, connections to the user, the recommended activity, or some combination thereof in developing the one or more recommendations.

The management interaction module 230 associates users of the life management system 140 with one or more assistants. Assistants may be automatically associated to users of the life management system 140, manually selected by the users, or some combination thereof.

Additionally, in some embodiments, users of the life management system 140 may configure one or more user controls, e.g., via the client device 105, that control how much snapshot information is be provided to the assistants, third party service providers 120, and other users of the life management system 140.

The management interaction module 230 receives requests for snapshot information associated with users of the life management system 140 from one or more assistant devices 125, client devices 105, or some combination thereof. The management interaction module 230 provides some or all of the requested snapshot information to the requesting one or more assistant devices 125, one or more client devices 105, or some combination thereof, in accordance with user controls of users associated with the requested snapshot information.

In some embodiments, portions of snapshot information provided to an assistant device 125, a client device 105, or both, may be displayed via one or more graphical user interfaces ("GUIs").

In one embodiment, one or more GUIs display some or all of the snapshot information associated with the user, e.g., an avatar, a momentum gauge indicating a momentum level, a user name, social data (e.g., calendar information), one or more health parameters, one or more analytical graphs of one or more health parameters, one or more recommendations, portions of biotelemetry data, portions of activity data, some other portion of snapshot information, mood information, portions of a user's calendar, or some combination thereof. Additionally, in some embodiments, the one or more GUIs display, some or all of the snapshot information associated with a plurality of users. For example, an assistant may be able to concurrently view snapshot information associated with different users of the life management system 140. Discussed in detail below with respect to FIGS. 3-8 are example embodiments of some of the one or more GUIs.

Figure 14A:
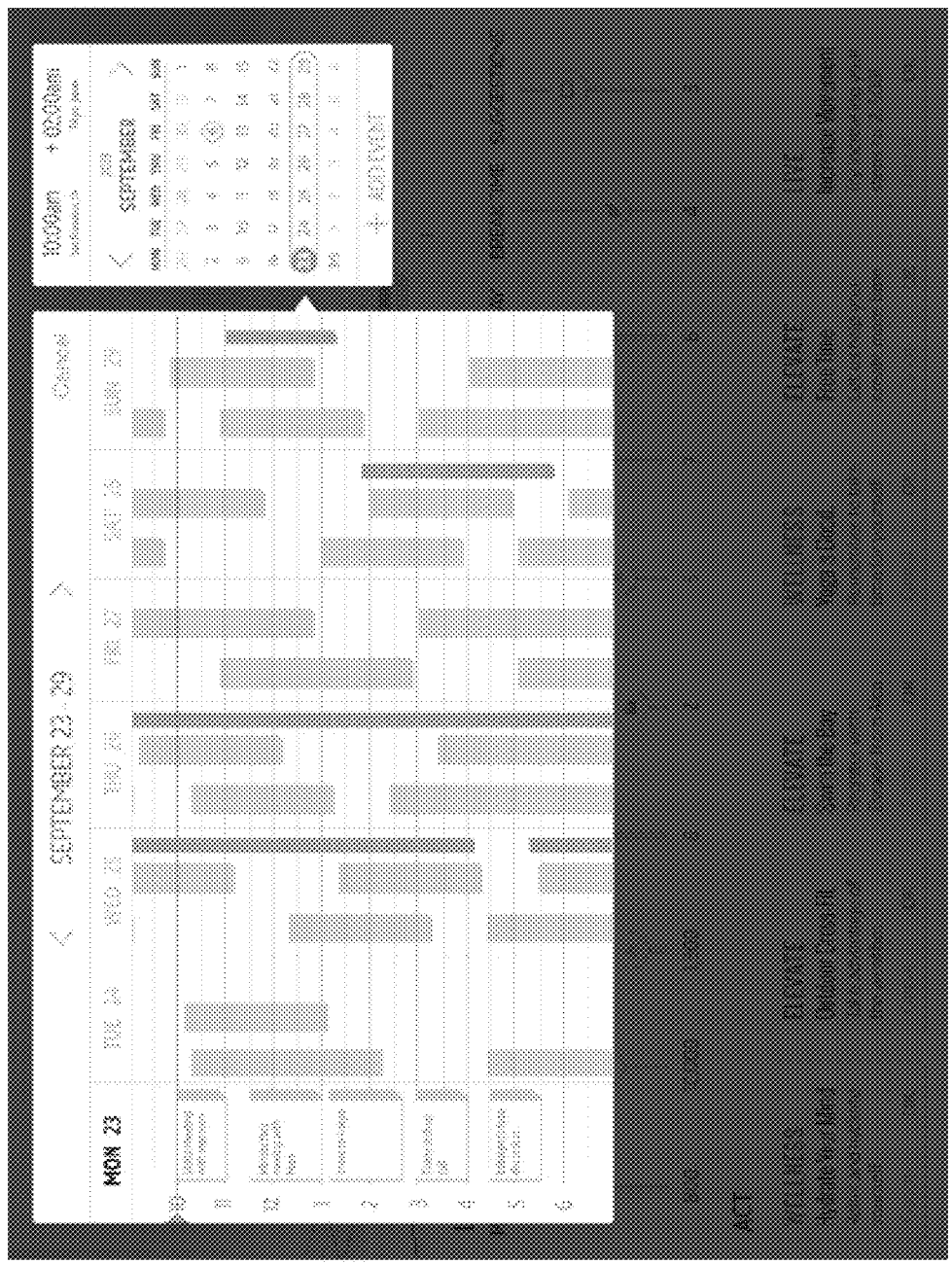
FIGS. 14A-C illustrate an example of a user interface displayed by a client device and/or an assistant device showing basic snapshot information in a calendar associated with a user of a life management system according to an embodiment.
Figure 14B:
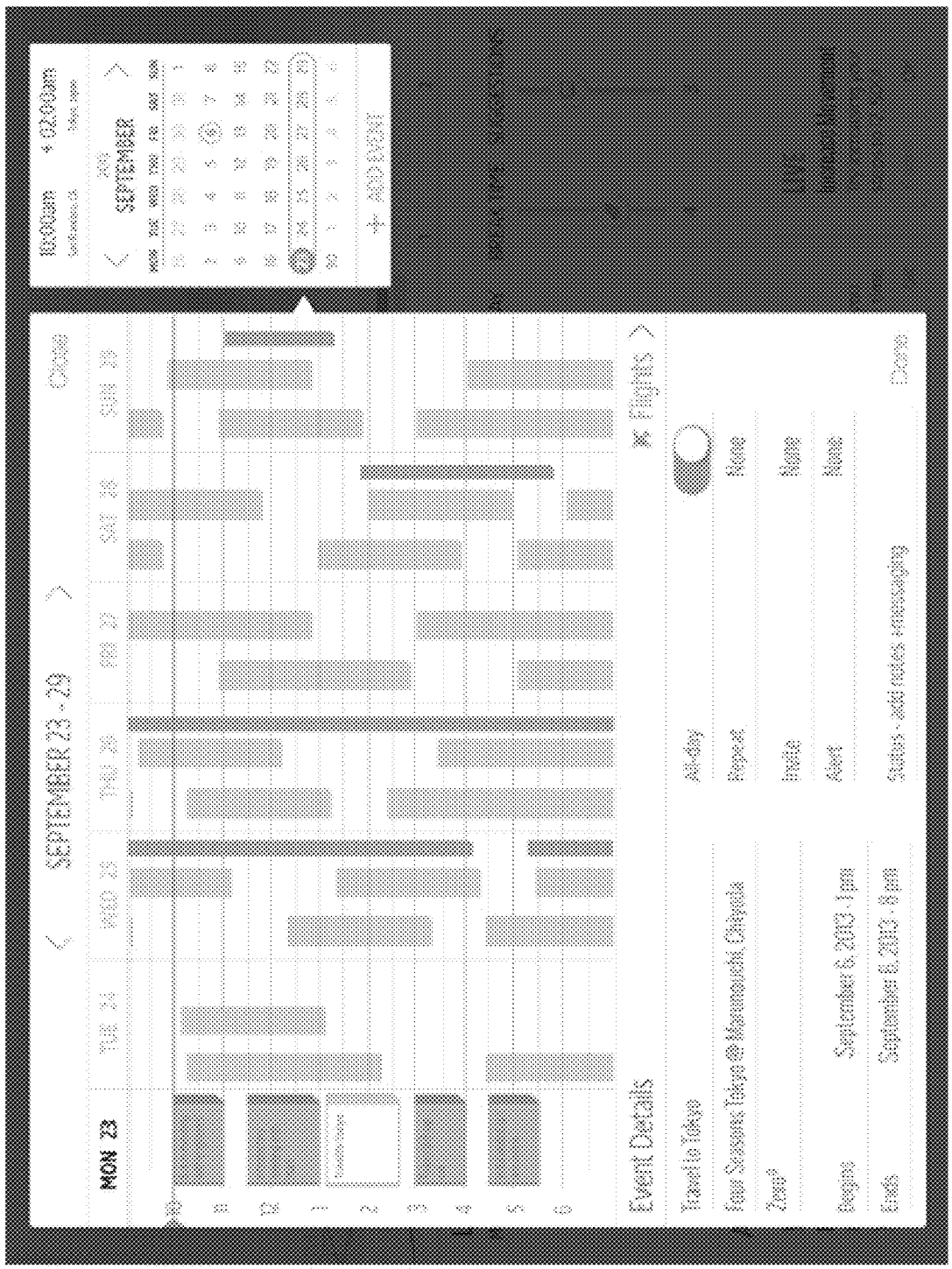
Figure 14C:
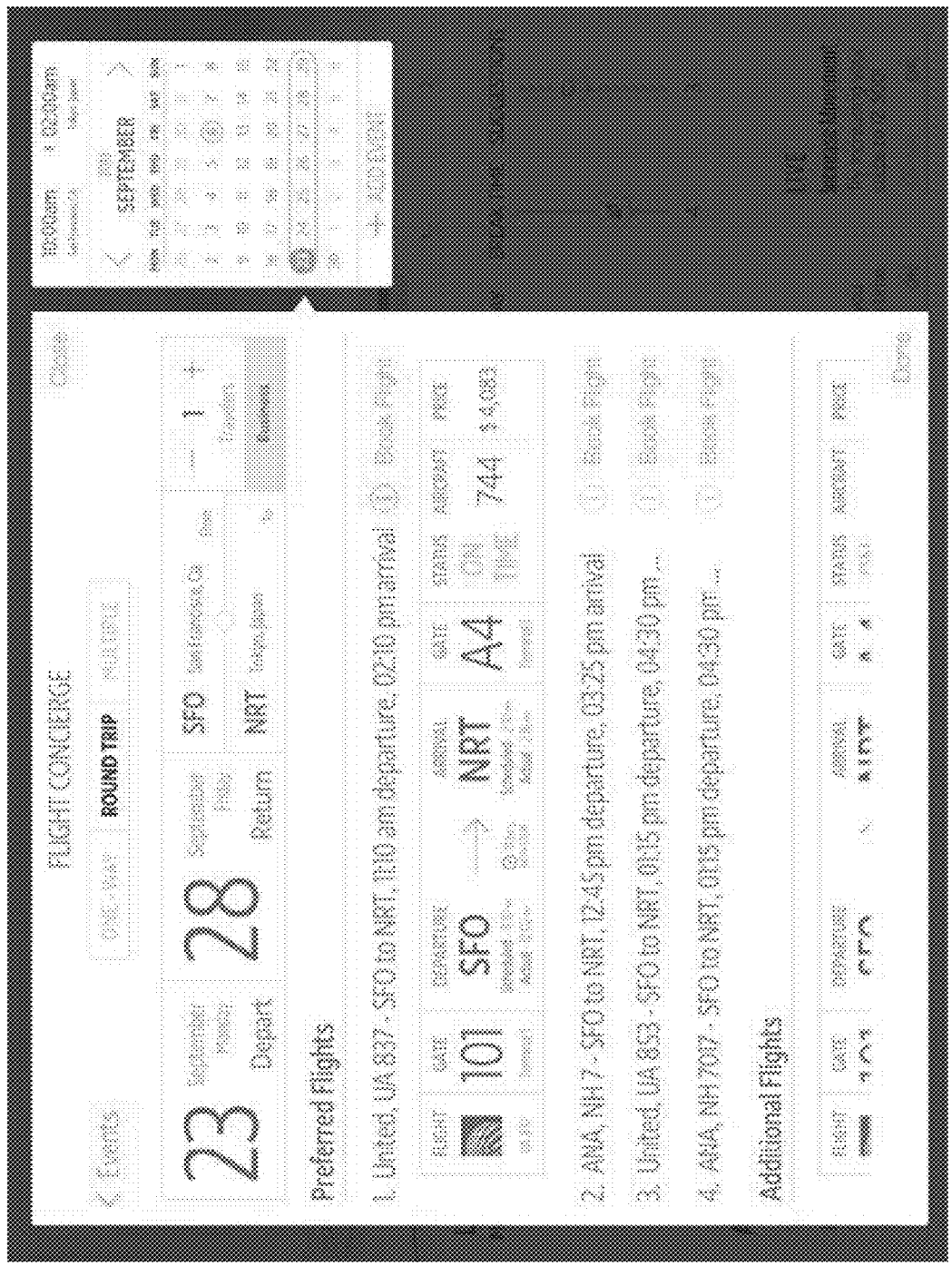

Additionally, in some embodiments, multiple GUIs may be concurrently be displayed to the user, as shown in for example, FIGS. 14A-C. For example, a GUI presenting a calendar in a monthly format—that allows the user to select a specific week, and/or day. Responsive to the selection of a particular week/day a second GUI may concurrently be presented to the user that displayed a detailed view of the selected area.

In some embodiments, the detailed view may be responsive to additional selections that request the life management system 140 perform an additional action. For example, a single GUI may initially be presented to the user that displays a user's calendar for a particular month. Responsive to the user selecting a particular day within the month, additional details of the week including the selected day are concurrently presented in a second GUI. Additionally, in some embodiments, the selected day may also display an expanded view of one or more calendar entries in relation to other calendar entries displayed for the rest of the week. Response to a selection of a particular calendar entry one or more additional details may also be displayed. For example, for a calendar entry associated with travel—there can be an option to select flights. Responsive to a selection of the select flights option, the GUI may display one or more possible flight options.

An assistant may analyze the information presented via the one or more GUIs to develop actionable information associated with the user. Actionable information is information associated with an action or recommendation that has been approved by an assistant associated user. Actionable information may be, for example, a recommendation generated by the recommendation module 225, a recommendation generated by the recommendation module 225—but modified by the assistant, a new recommendation created by the assistant, instructions to perform an action authorized by the assistant, a message (e.g., text, image, video, or some combination thereof) to the user, instructions to purchase a service or good associated from the third party service provider 120, update social data (e.g., calendar) associated with a user, or some combination thereof. For example, a health coach viewing a portion of snapshot information associated with the user may recommend an additional workout, the type of workout, the location of the workout, a proposed time for the workout, etc., via the assistant device 125. The management interaction module 230 receives the actionable information from the assistant device 125.

Additionally, in some embodiments, actionable information may include a container or package of information that an assistant may push to the user's client device 105. The container or package of information may include details like expected traffic during a particular time, suggestions of routes to take to drive to meeting and avoid traffic, a pick-up location for others the user may need to pick up to take to the meeting, travel data associated with the meeting (flight, hotel information), suggested restaurants near the meeting location, suggested stores at which to pick up supplies for the meeting along the way, links that provide more information associated with the meeting, among a variety of other pieces of information, a package of information about wellness (e.g., such as a list of all of the things a user should bring to his massage appointment, and suggestions of nearby places the user can pick up additional items needed), some other actionable information, or some combination thereof. Thus, the calendar entries/invites provided can include a rich, animated data set that is actionable.

The card generation module 235 generates one or more cards for presentation to one or more users of the life management system 140 using the users' associated snapshot information, actionable information, one or more advertisements, one or more recommendations, or some combination thereof. The card generation module 235 may generate a card, e.g., when an event associated with a calendar entry is set to begin in a certain period of time, one or more health parameters of the user are below a certain threshold, to suggest an advertisement for a good or service potentially of interest to the user, responsive to a request from an assistant device 125, responsive to a request from an event owner of a calendar entry, etc. The card generation module 235 provides the one or more cards generated for a user of the life management system 140 to the client device 105 associated with the user.

A card may include, for example, a card identifier, a general recommendation, one or more problem details, one or more recommendation details, a reminder (e.g., movie starts in 10 minutes), or some combination thereof. A card identifier identifies the type of card. For example, a card identifier may be a momentum alert, a calendar update, you may like this, event reminder, 'Be Fit,' 'Be Effective,' 'Be Aware,' some other action item, etc. A 'Be Fit' card identifier is associated with cards relating to physical and/or nutritional tasks (e.g., physical activity, hear rate, sleep, blood pressure, doctor's visit, eating habits, etc.). A 'Be Effective' identifier is associated with cards relating to social and/or occupational tasks (e.g., quality time with friends & family, meeting new people, volunteering, donating, work—life balance, efficient meetings, being punctual, referring friends, etc.). A 'Be Aware' identifier is associated with cards relating to emotional and/or environmental tasks (e.g., positive attitude, time management, breathing exercises, setting priorities, life balance, turn of lights, recycling, voting, volunteering, etc.). The general recommendation is a summary of the recommendation. General recommendations may be, for example, take a quick break, take a nap, drink water, reduce your calorie intake, or any other message that generally describes the recommendation. The one or more problem details include specific snapshot information (e.g., heart rate, hydration, sleep pattern, etc.). In some embodiments, the one or more problem details may include one or more icons that correspond to snapshot information (e.g., portions of biotelemetry data, activity data, health parameters, etc.) that is outside a preferred range. An icon may be, for example a heart with an arrow pointing upward to represent a rapid heart rate, a water droplet with a downward facing arrow to represent low hydration, etc. Additionally, the card generation module 235 may alter the icons (e.g., change color, shape, etc.) to indicate the present state of the user. The one or more recommendation details propose possible solutions to the identified problem. For example, if a user is dehydrated, the recommendation details may include a suggestion to drink water, visit the user's favorite juice bar, etc. Additionally, in some embodiments, the one more recommendation details may present one or more advertisements associated with solving the problem (e.g., a discount coupon for a local juice bar). The card generation module 235 is configured to provide one or more cards associated with a user of the life management system 140 to their associated client device 105. An example card is discussed below with regard to FIG. 9.

The action module 240 performs one or more actions, in accordance with the user controls of a user of the life management system 140, using the snapshot information, the actionable information, requests from one or more client devices 105, or some combination thereof. The action module 240 may, for example, instruct the social interaction module 215 to update a user's social data (e.g., calendar), coordinate with the third party service provider 120 to obtain a good and/or service, utilize snapshot information associated with the user in obtaining a good and/or service for the user, shift tasks among different entities in the life management environment 100, use conditions in one part of the life management environment 100 to set conditions in another part of the life management environment 100, automatically performing one or more actions in accordance with a user's user controls, some other action, or some combination thereof, based in part on snapshot information and/or actionable information associated with the user.

As noted above, in one embodiment, the action module 240 is able to use conditions in one part of the life management environment 100 to set conditions in another part of the life management environment 100. For example, the action module 240 may use geographic location information associated with a client device 105 associated with a user to set time parameters for another client device 105 (e.g., a wearable computer or wristband) associated with the user. In another embodiment, the action module 240 automatically changes one or more recommendations and/or scheduled events based on one or more health parameters associated with the user. For example, the action module 240 may recommend to the user a direct flight versus a flight with a connection if one or more health parameters of the user are below an associated threshold. In an additional embodiment, the action module 240 may notify an assistant associated with the user when the power level of the client device 105 associated with the user drops below a power threshold value.

As noted above, in one embodiment, the action module 240 is able to shift tasks between entities in the life management environment 100. For example, the action module 240 may automatically shift data among different client devices 105 associated with a user of the life management system 140. In one embodiment, the action module 240 monitors the power levels of a plurality of client devices 105 associated with a user. The action module 240 detects when the power level of one client device 105 drops below a threshold value (e.g., indicating a low batter level). The action module 240 may then automatically transfer some data items (e.g., a To Do list) from the client device 105 with the low power threshold to another client device 105 associated with the user that has an adequate power level. In another embodiment, the action module 240 may select an image, and push the selected image to a client device 105 based on the geographic location information associated with the client device 105. For example, sending an image of a sunrise in Seattle to a client device 105 that is located in Seattle.

In some embodiments, the action module 240 determines whether a conflict exists between locations associated with calendar entries in a calendar. A conflict occurs when there is not enough time to travel between one location associated with one calendar entry to another location associated with a different calendar entry. The action module 240 determines a route based on location information associated with the calendar entries. The action module 240 calculates optimal travel time between the location associated with different calendar entries using the determined route, the locations of the event described in the calendar entries, the location of the client device 105 associated with the user, travel conditions, weather data, or some combination thereof. If the calculated travel time is such that it the user is projected to not arrive at the estimated time, the action module notifies the user. Additionally, in some embodiments the action module updates the calculated travel time in real time. If the calculated travel time is such that it the user is projected to not arrive at the estimated time, the action module may instruct the social interaction module 215 and/or the card generation module 235 to notify the user, notify other participants in the calendar event, or some combination thereof.

The mood module 245 monitors mood information associated with various users of the life management system 140. The mood module 245 provides mood information associated with a user, in accordance with the user's user controls, to one or more entities of the life management environment 100. In some embodiments, the mood information may be associated with different moods of the user over a particular period of time (e.g., hourly, daily for the last week, etc.). In some embodiments, the mood information is automatically pushed to, e.g., one or more associated assistants (e.g., to the assistant device 125), one or more client devices 105 associated with the user, one or more client devices 105 associated users who are connected to the user, or some combination thereof.

Additionally, in some embodiments, a client device 105 associated with some other user and/or an assistant device 125 may request the mood of the user from the mood module 245. The other user and/or assistant may then make a determination on whether to interact with the user based on the mood information associated with the user.

Additionally, in some embodiments, a user may indicate, via their user controls, that one or more other users of the life management system 140 are trusted users. The mood module 245 then designates the one or more other users as trusted users, such that the trusted users may provide mood information to other users of the life management system 140.

Figure 3:
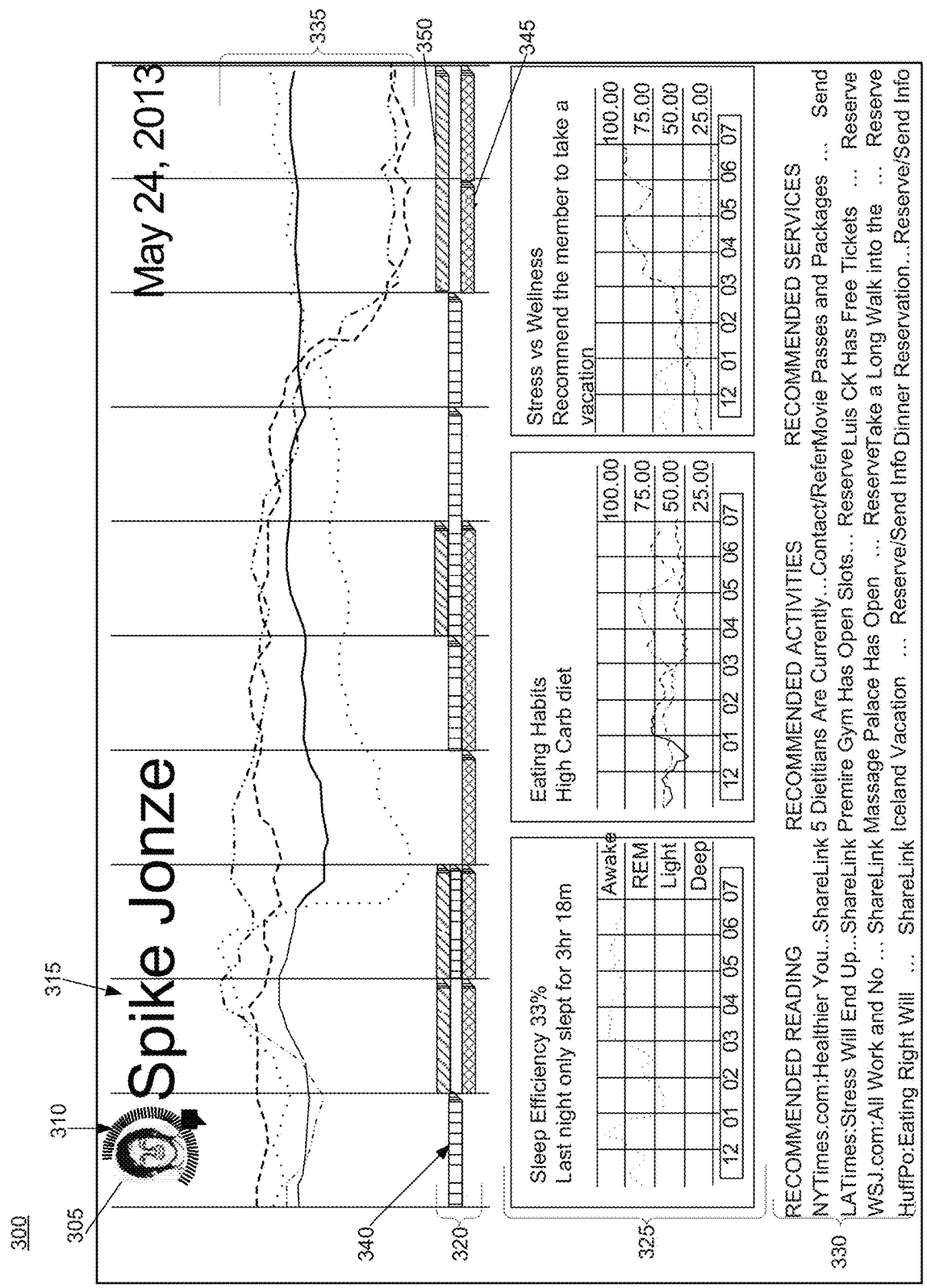
FIG. 3 illustrates an example of a user interface displayed by an assistant device and/or client device showing a detailed user snapshot associated with a user of a life management system according to an embodiment.

FIG. 3 illustrates an example of a user interface 300 displayed by the assistant device 125 and/or client device 105 showing a detailed user snapshot associated with a user of the life management system 140 according to an embodiment. The user interface 300 includes an avatar of the user 305, a momentum gauge 310, a name of the user 315, calendar information 320, analytical graphs 325, recommendations 330, and health parameters 335. The momentum gauge 310 presents a momentum score associated with the user. The calendar information 320 includes displays one or more calendar entries associated with the user. In this example, the calendar entries run from left to right, such that time progresses throughout the day (i.e., May 24, 2013) from right to left.

Figure 12:
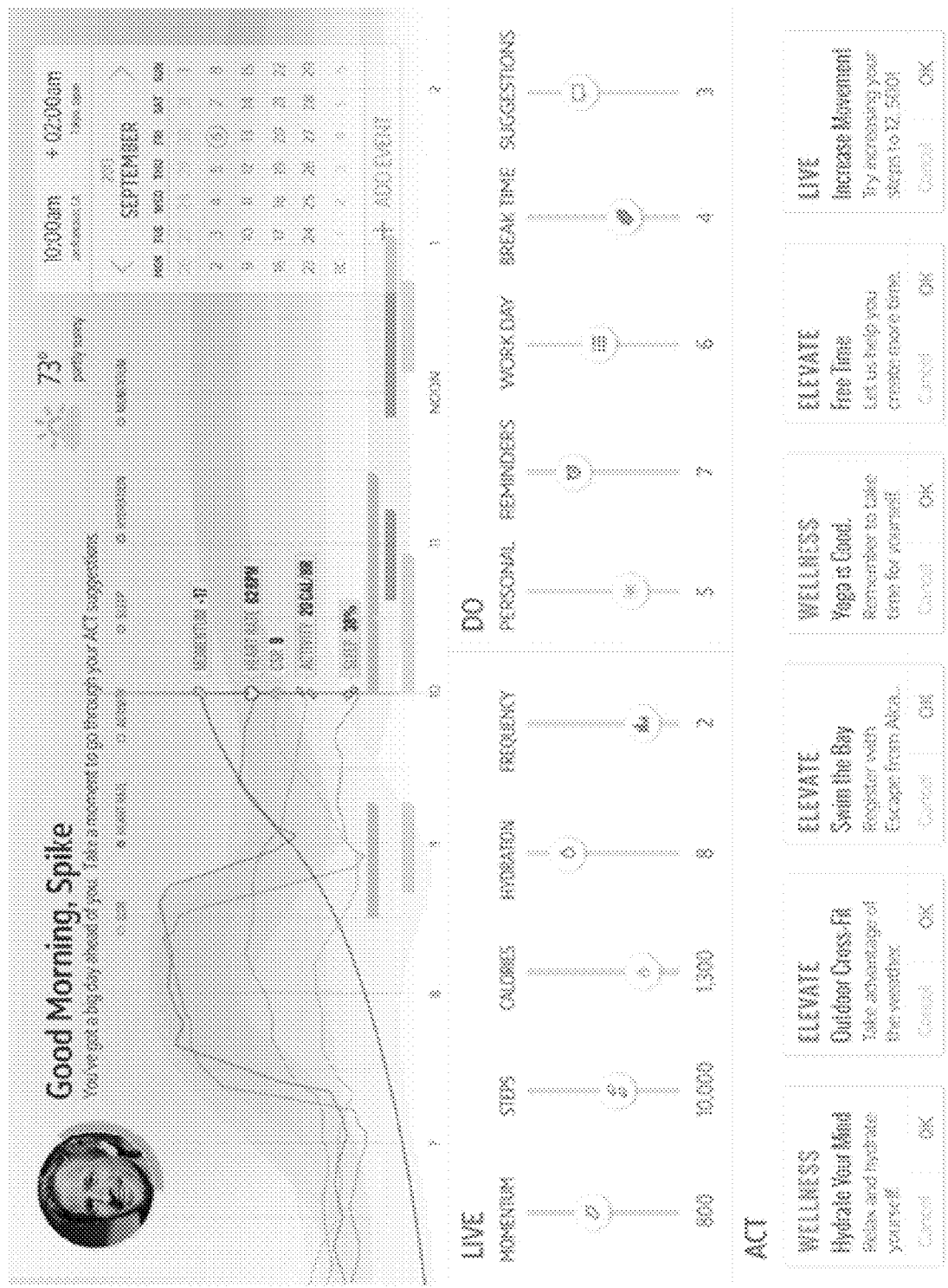
FIG. 12 illustrates another example of a user interface displayed by an assistant device showing a detailed user snapshot associated with a user of a life management system according to an embodiment.

Additionally, in this example, the user as one calendar entry 340 scheduled for a particular time, and is double booked with calendar entries 345 and 350 over a different time slot. In some embodiments, the interface 300 includes information about multiple users for an assistant, such as all of the users on the team supported by an executive assistant or being managed by a health coach. The assistant can thus view summaries of each person's schedule, review each person's momentum gauge, have access to each person's current biotelemetry data and/or activity data, among other data. The assistant can use this information in assisting each user. For example, if member 1 of the assistant's team doing poorly in terms of momentum or has mood data showing he is in a bad mood, the assistant can cancel some of member 1's meetings and schedule a yoga session. If member 2's data shows her heart rate has been elevated for a period of time, the assistant can send a suggestion regarding relaxation techniques. Additionally, alternative views exist, for example, as shown in FIG. 12 that illustrates another example of a user interface displayed by an assistant device 125 and/or client device 105 showing a detailed user snapshot associated with a user of a life management system according to an embodiment.

Figure 4:
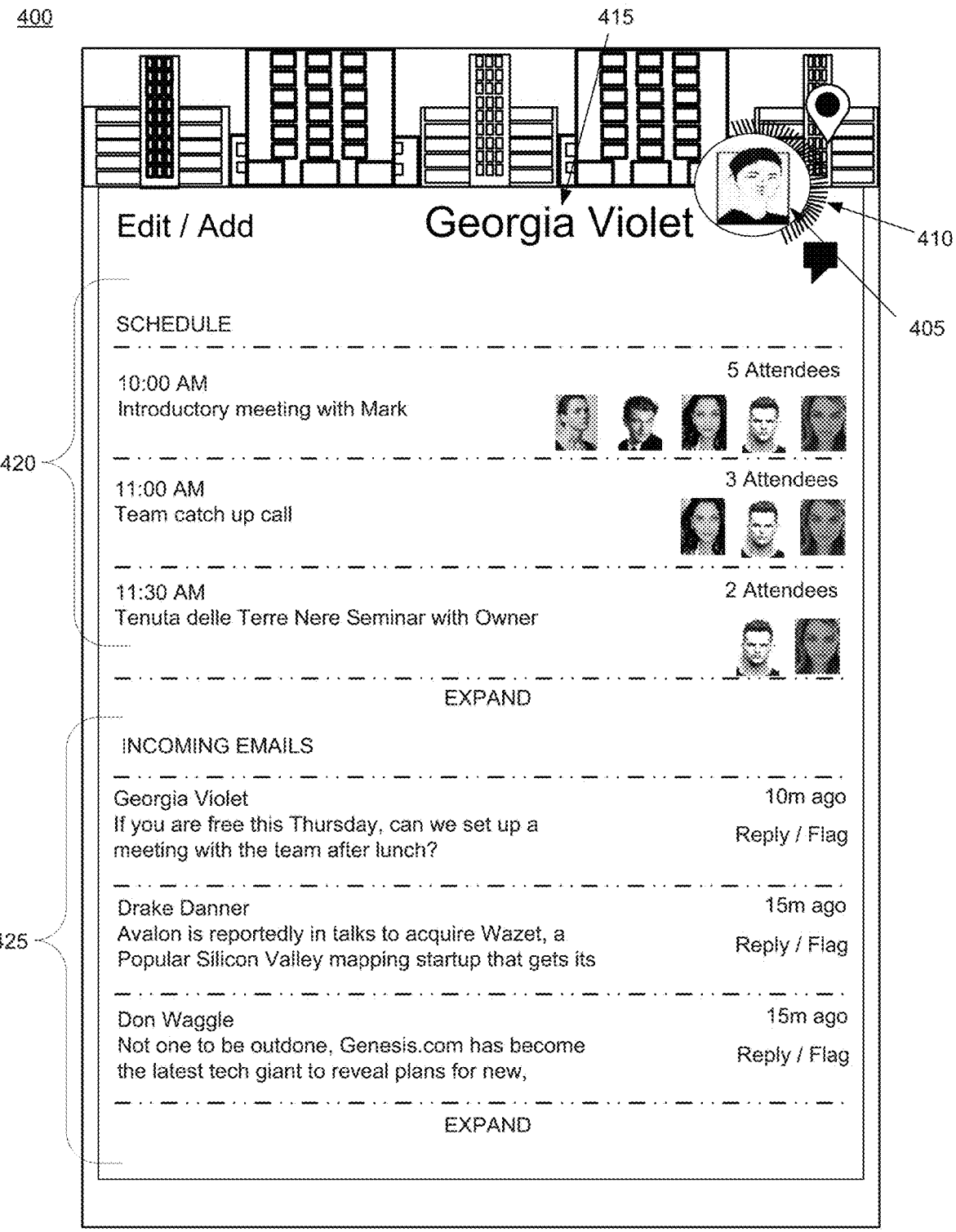
FIG. 4 illustrates an example of a user interface displayed by an assistant device and/or a client device showing a basic user snapshot associated with a user of a life management system according to an embodiment.

FIG. 4 illustrates an example of a user interface 400 displayed by the assistant device 125 and/or a client device 105 showing a basic user snapshot associated with a user of the life management system 140 according to an embodiment. The user interface 400 includes an avatar of the user 405, a momentum gauge 410, a name of the user 415, calendar information 420, and emails 425.

Figure 5:
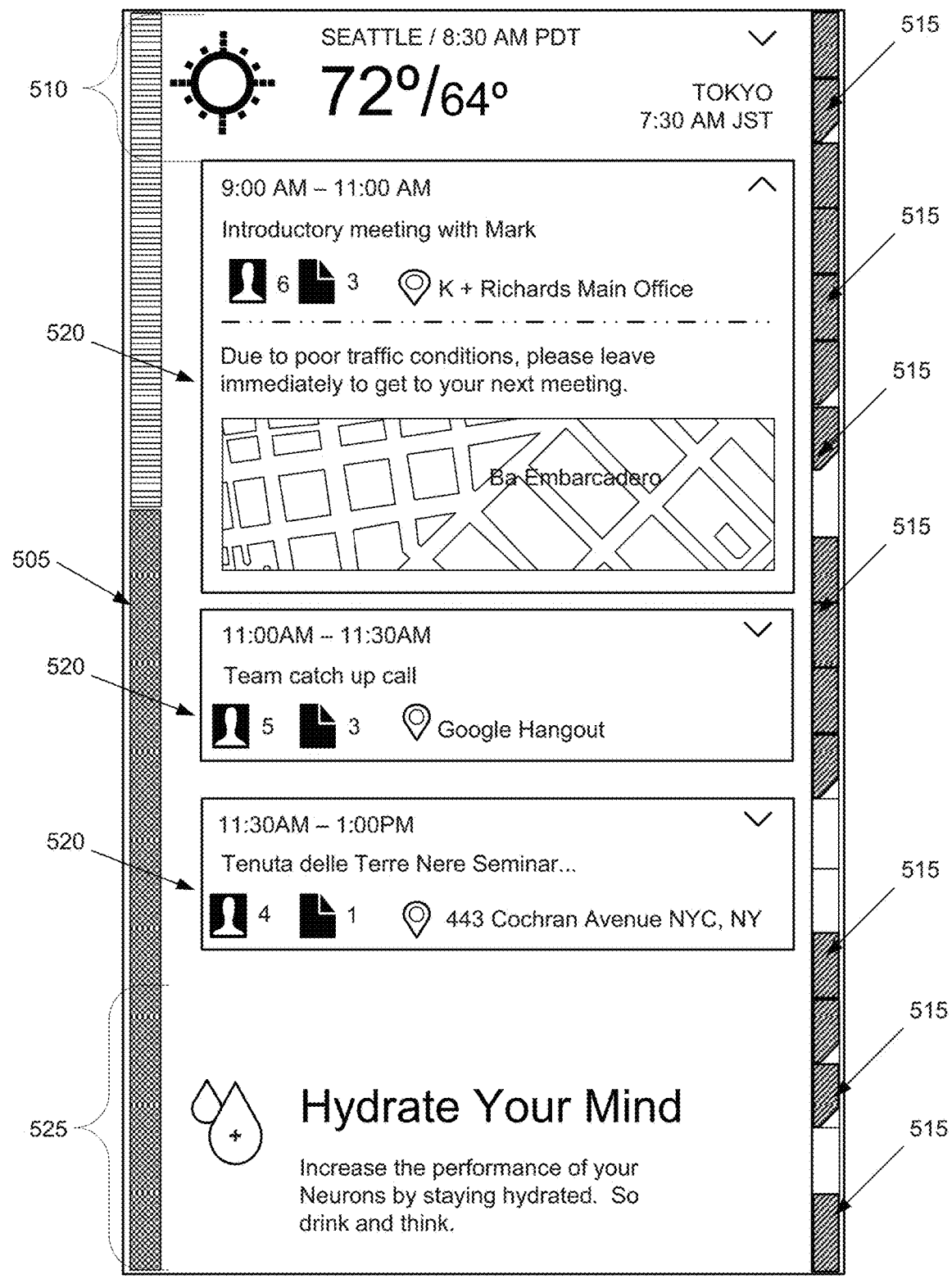
FIG. 5 illustrates an example of a user interface displayed by a client device showing a portion of snapshot information associated with a user of a life management system according to an embodiment.
Figure 13:
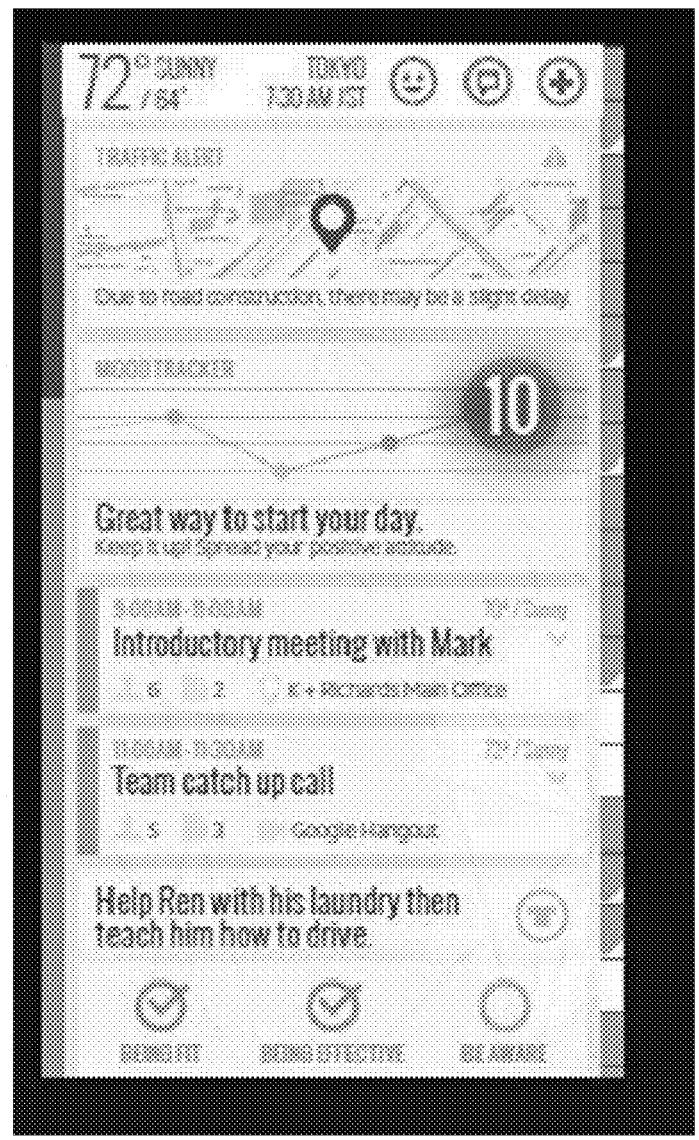
FIG. 13 illustrates another example of a user interface displayed by a client device showing a portion of snapshot information associated with a user of a life management system according to an embodiment.

FIG. 5 illustrates an example of a user interface 500 displayed by a client device 105 showing a portion of snapshot information associated with a user of the life management system 140 according to an embodiment. The user interface 500 includes a momentum gauge 505, general information 510, calendar entries 515, and detailed views 520 of corresponding calendar entries 515, and a recommendation 525. In some embodiments, a user interface may also include mood information as shown in FIG. 13.

Figure 6:
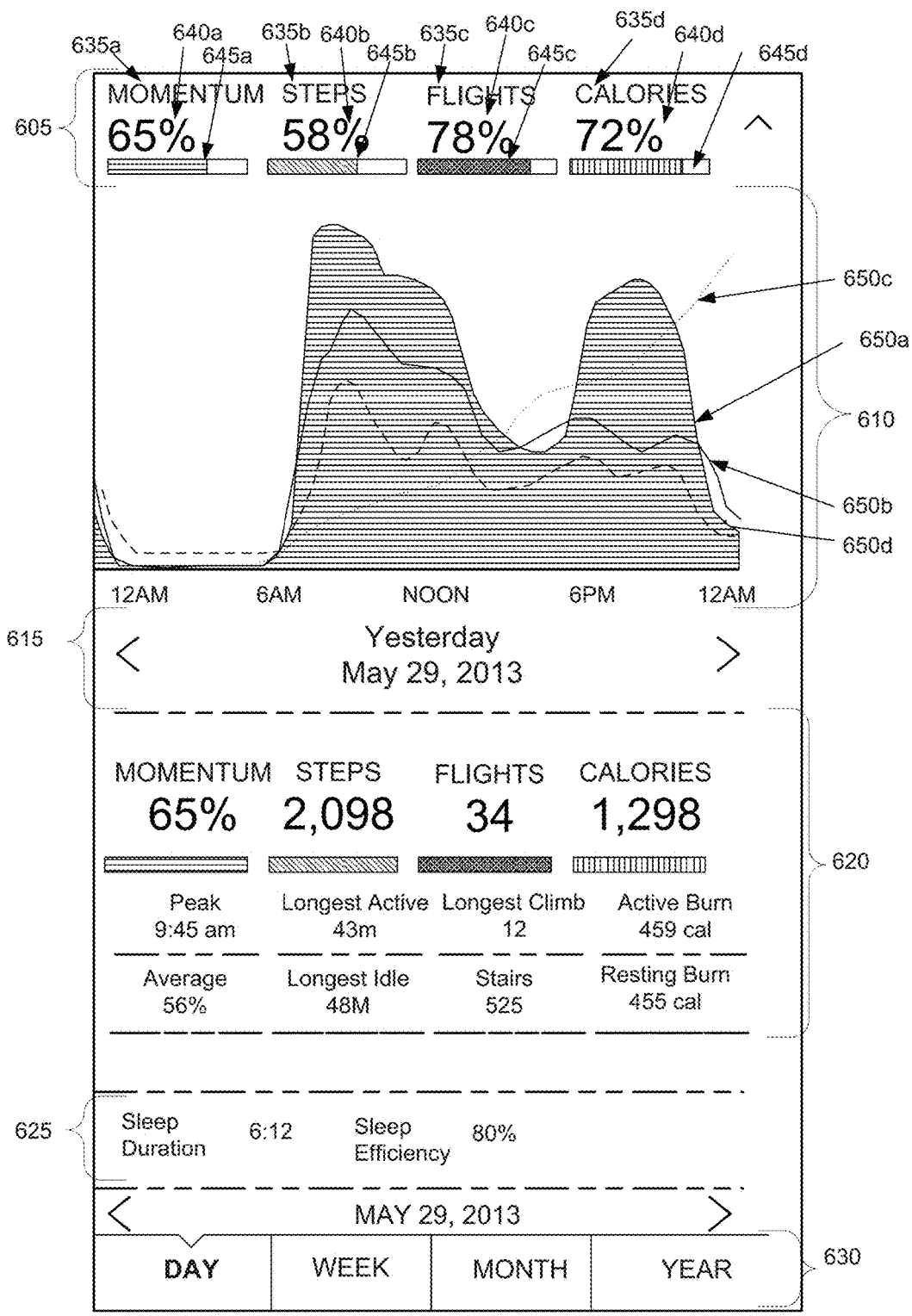
FIG. 6 illustrates another example of a user interface displayed by a client device showing portions of snapshot information associated with a user of a life management system according to an embodiment.

FIG. 6 illustrates another example of a user interface 600 displayed by a client device 105 showing portions of snapshot information associated with the user of a life management system 140 according to an embodiment. The user interface 600 includes a health parameter section 605, analytical graph section 610, a date section 615, a health parameters details section 620, a sleep information section 625, and a time aggregate control 630. In this example, the health parameter section 605 displays a plurality of health parameter identifiers 635a-635d, their associated scores 640a-640d, and graphical indications 645a-645d of the scores 640a-640d. In this example, the analytical graph section 610 includes graphs 650a-650d, where graph 650a is associated with the health parameter identifier 635a, graph 650b is associated with the health parameter identifier 635b, graph 650c is associated with the health parameter identifier 635c, and graph 650d is associated with the health parameter identifier 635d. The health parameters details section 620 includes additional information about the displayed health parameters. The time aggregate control 630 allows a user to select what time interval is used to calculate the displayed snapshot information. For example, in this example a day is selected, and the associated snapshot information is taken from a single day (i.e., May 29, 2013). If the user were to select some other time interval, e.g., a week, the displayed snapshot information would cover a weeks' time (e.g., the last seven days—or some other seven day period selected by the user).

Figure 7:
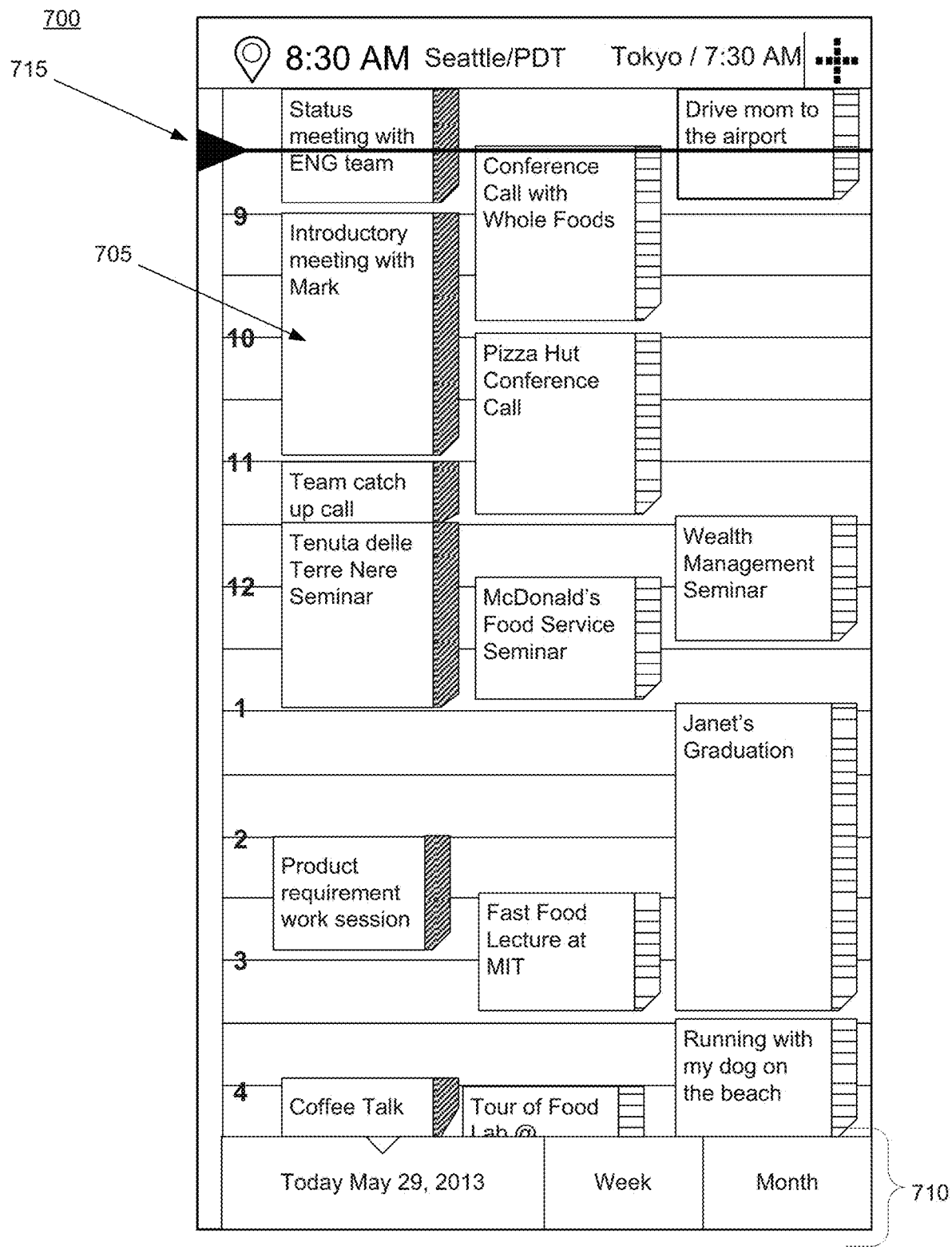
FIG. 7 illustrates an example of a user interface displayed by a client device showing basic snapshot information in a calendar associated with a user of a life management system according to an embodiment.

FIG. 7 illustrates an example of a user interface 700 displayed by a client device 105 showing basic snapshot information in a calendar associated with a user of the life management system 140 according to an embodiment. The user interface 700 includes a plurality of general calendar entries 705, a view control 710, and a time indicator 715. The user interface 700 may receive a selection from the user to expand one or more general calendar entries 705. Additionally, the user interface 700 may receive a selection from the user to view a larger or small section (e.g., a single day, a week, a month, etc.) of the calendar via the view control 710. The time indicator 715 graphically illustrates the local time (e.g., 8:30 am). In addition, the calendar entries 705 in FIG. 7 correspond with the tabs 515 shown in the FIG. 5 calendar summary view. For example, the top four tabs each labeled 515 in FIG. 5 correspond with the top four calendar entries 705 on the left-most calendar column in FIG. 7. The break in the calendar of FIG. 7 from a little before 2 pm until 3 pm is illustrated in the view of FIG. 5 as an empty spot before the fifth tab labeled 515. Thus, the user can view the interface of FIG. 5 and see in short-hand using tabs 515 what is coming up on his calendar and when he has breaks, alongside the view of his momentum gauge 505 showing his current level of momentum (bar 505 moves up or down corresponding to momentum level) and a summary of some of the next few calendar items coming up. The user can use the FIG. 7 interface to see the details of the calendar entries 705 corresponding to the tabs 515.

Figure 8:
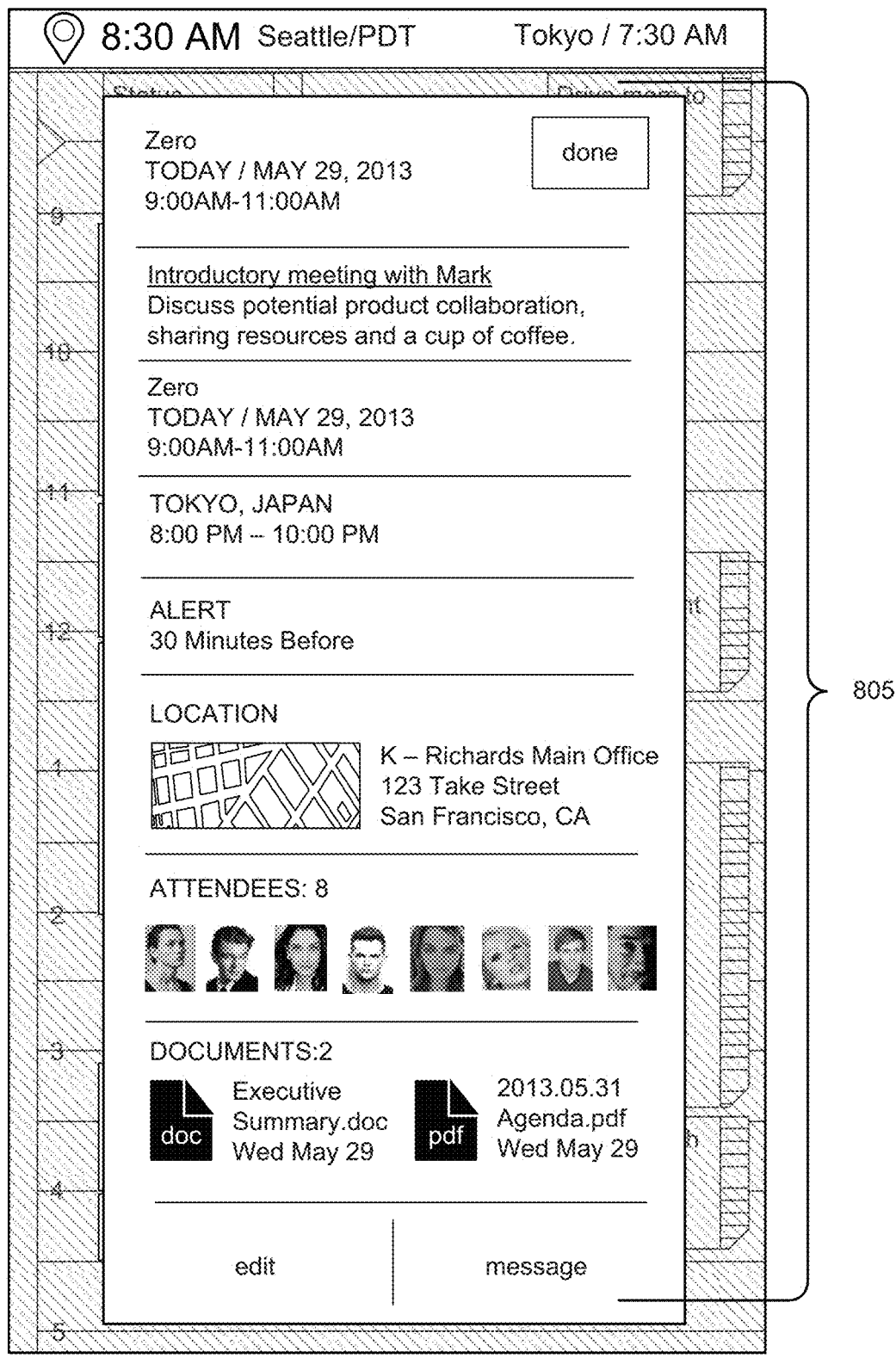
FIG. 8 illustrates an example of a user interface displayed by a client device showing an expanded general calendar entry associated with a user of a life management system according to an embodiment.

FIG. 8 illustrates an example of a user interface 800 displayed by a client device 105 showing an expanded general calendar entry associated with a user of the life management system 140 according to an embodiment. The user interface 800 displays the expanded general calendar entry 805. The expanded calendar entry 805 may include portions of snapshot information associated with the general calendar entry. FIG. 8 illustrates that a variety of different types of actionable information can be included in each calendar entry or invite, and this information might be provided by an assistant who has pushed this calendar entry out to the user's client device 105. The assistant can create a container or package of information that includes details like expected traffic during that time, suggestions of routes to take to drive to meeting and avoid traffic, a pick-up location for others the user may need to pick up to take to the meeting, travel data associated with the meeting (flight, hotel information), suggested restaurants near the meeting location, suggested stores at which to pick up supplies for the meeting along the way, links that provide more information associated with the meeting, among a variety of other pieces of information. In another example, the calendar entry is provided by a physician or coach of the user, and it includes a package of information about momentum, such as a list of all of the things a user should bring to his massage appointment, and suggestions of nearby places the user can pick up additional items needed. Thus, the calendar entries/invites provided can include a rich, animated data set that is actionable.

Figure 9:
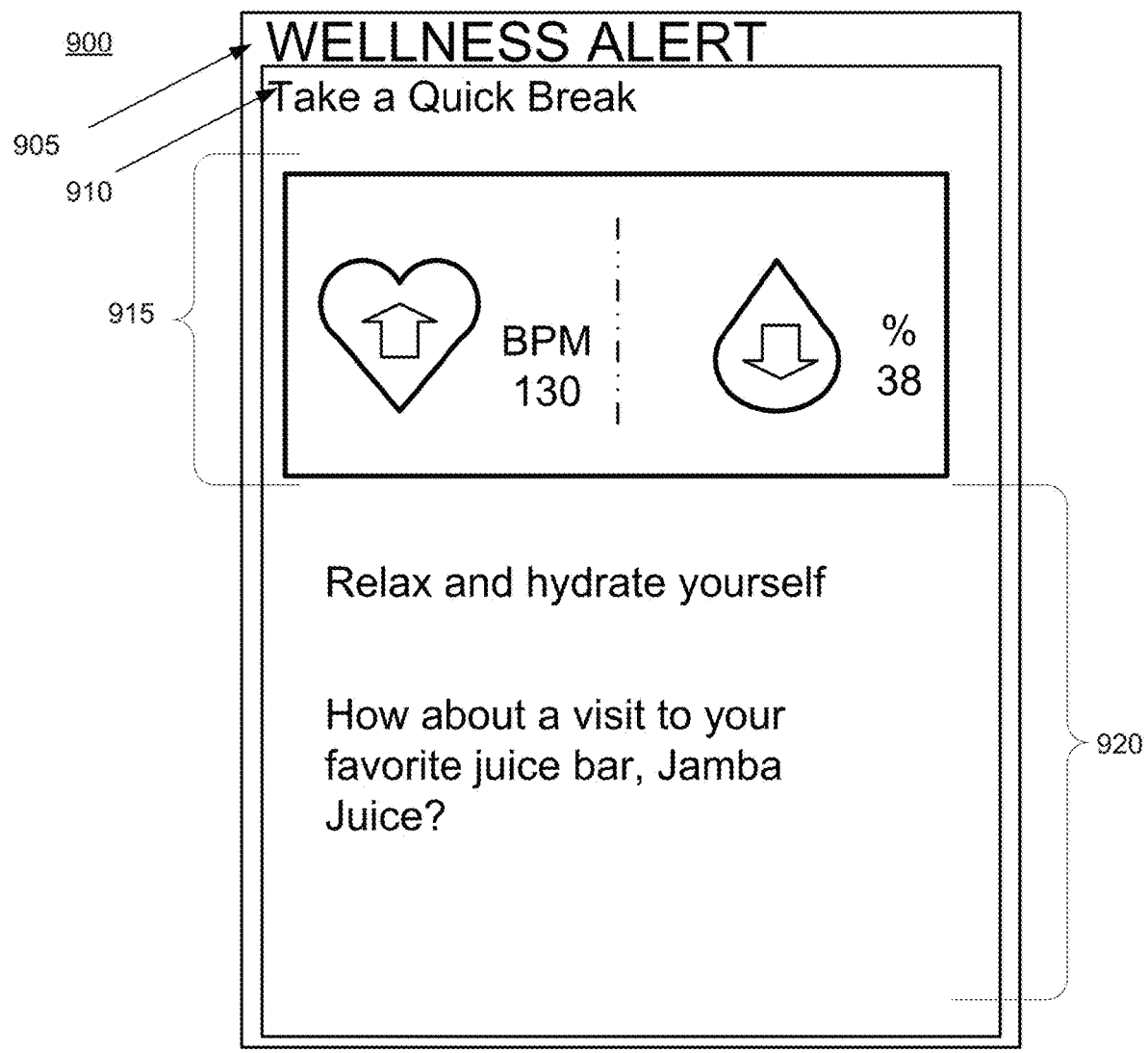
FIG. 9 illustrates an example of a card displayed by a client device to an associated user of a life management system according to an embodiment.

FIG. 9 illustrates an example of a card 900 displayed by a client device 105 to an associated user of the life management system 140, according to an embodiment. The card 900 includes a card identifier 905, a general recommendation 910, problem details 915, and recommendation details 920.

Figure 10:
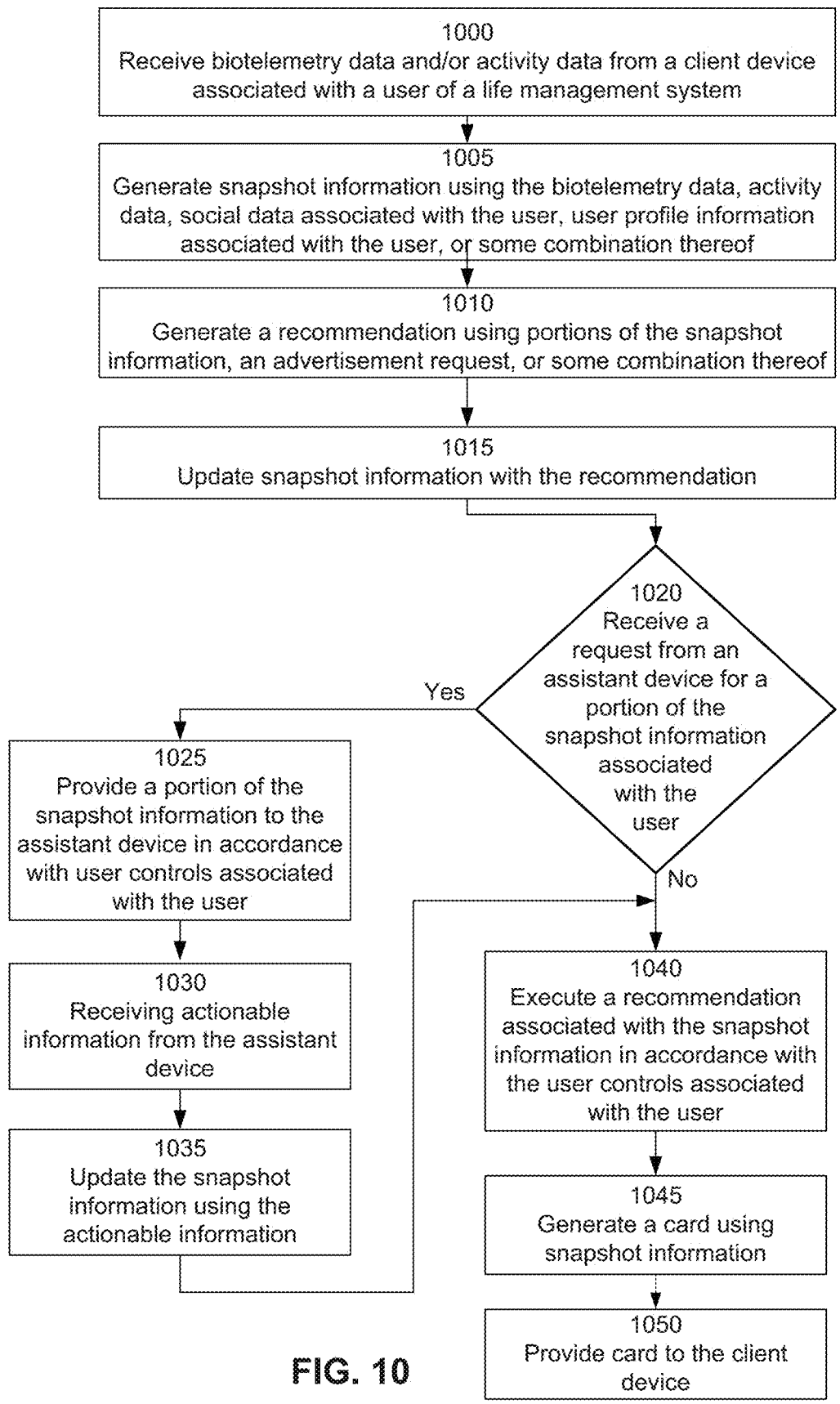
FIG. 10 is a flowchart illustrating the process for generating a card using snapshot information associated with a user of a life management system according to one embodiment.

FIG. 10 is a flowchart illustrating the process for generating a card using snapshot information associated with a user of the life management system 140 according to one embodiment. In one embodiment, the process of FIG. 10 is performed by the life management system 140. Other entities may perform some or all of the steps of the process in other embodiments. Likewise, embodiments may include different and/or additional steps, or perform the steps in different orders.

The life management system 140 receives 1000 biotelemetry data and/or activity data from a client device 105 associated with the user. The life management system 140 generates snapshot information using the biotelemetry data, the activity data, social data associated with the user, user profile information associated with the user, or some combination thereof.

The life management system 140 generates 1010 a recommendation using portions of the snapshot information, an advertisement request, or some combination thereof. In some embodiments, the life management system 140 generates a recommendation to improve one or more health parameters associated with the user using portions of the snapshot information. For example, the life management system may determine that a user's is overly stressed. The life management system 140 may then select an advertisement associated with reducing stress (e.g., for a massage, bed and breakfast, etc.). The life management system 140 then may incorporate the advertisement and a suggestion to reduce to user's stress level in a recommendation.

The life management system 140 updates 1015 the snapshot information with the one or more recommendations. If a request is received 1020 from an assistant device 125 for a portion of the snapshot information associated with the user, the life management system 140 provides 1025 the portion of snapshot information to the assistant device 125 in accordance with user controls associated with the user. The information may be presented via, for example, one or more graphical user interfaces that display portions of the received snapshot information. The assistant associated with the assistant device 125 may then analyze the snapshot information to develop actionable information. For example, the assistant may recommend an item to the user, want to purchase a good/service for the user, etc. The life management system 140 receives 1030 actionable information from the assistant device 125.

The life management system 140 updates 1035 the snapshot information using the actionable information. For example, the life management system 140 may update one or more recommendations in the snapshot information based on the actionable information (e.g., add one or more new recommendations, modify an existing recommendation, etc.).

The life management system 140 executes 1040 a recommendation associated with the snapshot information in accordance with the user controls associated with the user. In embodiments, where the life management system 140 does not have a sufficient authorization level to perform the action, the life management system 140 requests approval from the client device 105 to perform the action. Similarly, in embodiments, where the action was requested by the assistant and the assistant does not have sufficient authorization level to perform the action, the life management system 140 requests approval from the client device 105 to perform the action.

The life management system 140 generates 1045 a card using the snapshot information. For example, the card may present a health parameter that has a value below a certain threshold, a recommendation on how to improve the health parameter, and an associated advertisement for a good/service that may facilitate improvement of the health parameter. In another example, the card may be a request for the user to approve a suggested change to their calendar. In another example, the card may contain information reminding the user about a scheduled calendar entry.

Additionally, the in some embodiments, where the life management system 140 has already executed the action the card may be a notification that the action has been executed by the life management system 140 and/or the assistant.

The life management system 140 provides 1055, for display to the user, the card to the client device 105. In embodiments, where the card requests user approval of an action or recommendation described by the card, if the life management system 140 receives approval from the user, the process moves to step 1040.

Figure 11:
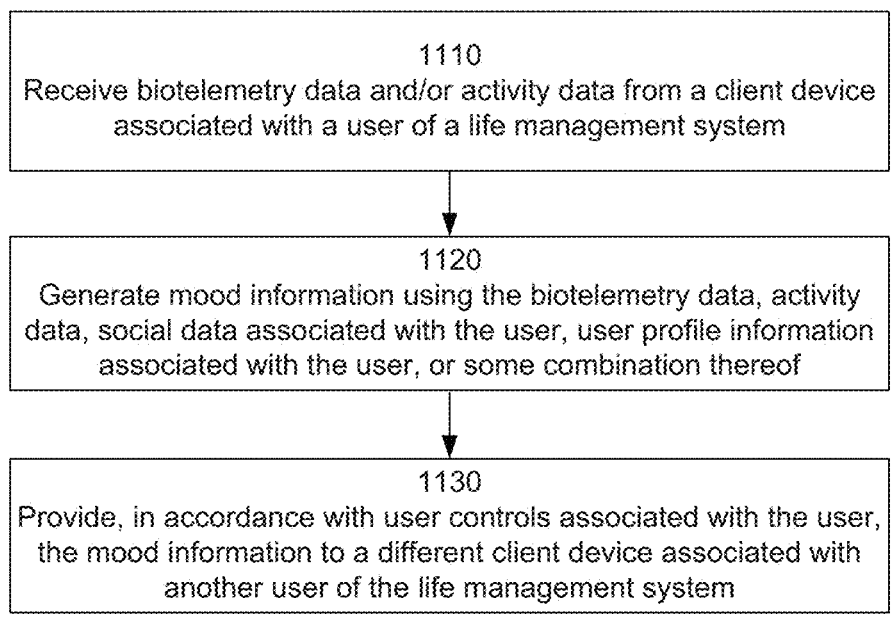
FIG. 11 is a flowchart illustrating the process for generating and managing mood information associated with a user of a life management system according to one embodiment.

FIG. 11 is a flowchart illustrating the process for generating and managing mood information associated with a user of the life management system 140 according to one embodiment. In one embodiment, the process of FIG. 11 is performed by the life management system 140. Other entities may perform some or all of the steps of the process in other embodiments. Likewise, embodiments may include different and/or additional steps, or perform the steps in different orders.

The life management system 140 receives 1110 biotelemetry data and/or activity data from a client device 105 associated with the user. The life management system 140 generates 1120 mood information using the biotelemetry data, activity data, social data associated with the user, user profile information associated with the user, or some combination thereof.

The life management system 140 provides, in accordance with user controls associated with the user, the mood information to a different client device 105 associated with another user of the life management system 140. In one embodiment, the life management system 140 may automatically push mood information associated with the user to other users of the life management system 140 in accordance with the user's user controls. In other embodiments, other users of the life management system 140 may request mood information associated with a user from the life management system 140 and/or some other trusted third party. The trusted third party and/or the life management system 140 then provide, in accordance with the user's user controls, the mood information to the requesting client device 105.

Additional Configuration Considerations

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non transitory, tangible computer readable storage medium and may include any embodiment of a computer program product or other data combination described herein.

The text of the abstract of one priority document is hereby repeated. A life management system receives data from a client device worn by a user, the data comprising biotelemetry data and activity data collected about a user wearing the client device. The life management system generates snapshot information using information from a group consisting of: the biotelemetry data, activity data, social data associated with the user, and user profile information associated with the user. The life management system generates a recommendation using portions of the snapshot information, and updates the snapshot information with the recommendation. The life management system executes a recommendation associated with the snapshot information in accordance with the user controls associated with the user.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon.

Accordingly, the disclosure of the embodiments is intended to be illustrative, but not limiting, of the scope of the disclosure, which is set forth in the following claims.

It will be understood that the present invention has been described above purely by way of example, and modifications of detail can be made within the scope of the invention.

Each feature disclosed in the description, and (where appropriate) the claims and drawings may be provided independently or in any appropriate combination.

Reference numerals appearing in the claims are by way of illustration only and shall have no limiting effect on the scope of the claims.

What is claimed is:

1. A computer implemented method for generating a recommendation on a device of a user of a life management system, the life management system comprising a processor configured to execute non-transitory machine readable instructions, wherein execution of the non-transitory machine readable instructions by the processor causes the life management system to:

receive data relating to the user, the user data comprising biotelemetry data received from a biotelemetry device configured to be worn by the user and collect one or more of the biotelemetry data and activity data via a wireless connection between the biotelemetry device and the life management system, the activity data collected about the user and social data of the user, the social data comprising calendar entries on a calendar for the user;

automatically change a graphical user interface of a display of the user device to represent a detected mood of the user based on the collected biotelemtry data and the activity data by changing at least one of a color scheme of the display or change the graphical user interface to include different types of information associated with the detected mood;

access the calendar on a client device of the user and a calendar on a client device of at least one other user by remotely connecting to the client device of the user and the client device of the at least one other user, wherein the at least one other user is identified as a contact by the life management system in a corresponding contact application of the client device of the user;

analyze the calendar on the client device of the user and the calendar on the client device of the at least one other user;

identify an open time slot in the calendar of the user that is common to an open time slot identified by the life management system in the calendar of the at least one other user;

generate an entry in the open time slot in the calendar of the user reserving the open time slot for a new activity and generate an entry in the open time slot in the calendar of the at least one other user reserving the open time slot for the new activity;

generate snapshot information using the biotelemetry data, the activity data and user profile information associated with the user;

determine a momentum score for the user using portions of the snapshot information;

compare the momentum score to a threshold value, and determine a requirement for the new activity based on the comparison;

develop a travel-related recommendation to both the user and the at least one other user based on the requirement, wherein the new activity is based on the travel-related recommendation;

engage with a third party service that is configured to carry-out the new activity associated with the travel-related recommendation;

automatically update an entry in the calender of the user with the new activity in the open time slot in the calendar of the user and an entry in the open time slot in the calendar of the at least one other user with the travel-related recommendation and information related to the third-party service.

2. The computer implemented method of claim 1, wherein the biotelemetry data comprises information related to at least one of: heart rate, calories burned, blood pressure, skin temperature, brain activity, hydration level, galvanic skin response, an optical skin and blood vessel dilation measurement, a blood glucose level, a blood oxygen level, a blood alcohol level, an electrocardiogram, an electroencephalogram, an electromyogram, a respiration rate, and a measure of stress.

3. The computer implemented method of claim 1, wherein the activity data comprises information related to at least one of: steps taken, stairs climbed, exercise intensity, pace, sleep pattern, a pedometer count, a measure of activity, a movement from an accelerometer, a movement from a gyroscope, a response to mechanical or electrical stimuli, a movement from an accelerometer, a movement from a gyroscope, a response to mechanical or electrical stimuli, a number of steps taken, a measure of calories used, an environment temperature, an ambient ultraviolet light level, an ambient $CO_2$ level and sleep duration.

4. The computer implemented method of claim 1, wherein the snapshot information generation further comprises using social data of the user, the social data comprising information related to at least one of: a calendar for the user, an interest of the user, one or more connections to the user, and a location of the user.

5. The computer implemented method of claim 1, wherein determination of the momentum score, further comprises determining values for one or more health parameters using portions of the snapshot information.

6. The computer implemented method of claim 1, wherein the travel-related recommendation is further based on at least one of an interest of the user, a schedule of the user, a geographical location of the user compared with a geographical location of the at least one other user, or a health of the user.

7. The computer implemented method of claim 1, further comprising:

receiving a request from an assistant to the user for a portion of the snapshot information associated with the user;

providing the portion of the snapshot information to the assistant in accordance with user controls associated with the user;

updating the snapshot information using actionable information received from the assistant;

wherein the actionable information comprises:

a new recommendation for the user, modifying the recommendation, adding a calendar entry to the user's calendar, purchasing a good, or purchasing a service.

8. The computer implemented method of claim 7, wherein the assistant is a health coach, a personal assistant, or a customer service representative.

9. The computer implemented method of claim 7, wherein providing the portion of the snapshot information to the assistant in accordance with user controls associated with the user, comprises:

providing a graphical user interface to the assistant that displays one or more health parameters, the momentum score for the user, analytical graphs for each of the displayed health parameters, and the recommendation.

10. The computer implemented method of claim 7, wherein providing the portion of the snapshot information to the assistant in accordance with user controls associated with the user, comprises:

providing a graphical user interface to the assistant that displays one or more calendar entries, one or more emails, and the momentum score for the user.

11. The computer implemented method of claim 1, further comprising:

providing a graphical user interface to the user that displays information selected from the group consisting of: calendar information associated with the user, one or more health parameters associated with the user, analytical graphs for each of the displayed health parameters, the recommendation, and a the momentum score.

12. The computer implemented method of claim 1, further comprising:
generating a card for presentation to the user, wherein the card includes data corresponding to the travel-related recommendation; and
providing the card to a client device of the user, and using the data to update icons on a graphical user display of the client device to correspond to the travel-related recommendation.

13. The method according to claim 1, the method further comprising:
determining a power level of a device of the user and a device of the at least one other user; and
transferring one or more of tasks and data items from the device of the user to the device of the at least one other user when the power level is below a predetermined threshold.

14. The method according to claim 13, wherein the at least one other user comprises at least two other users.

15. The computer implemented method according to claim 1, the method further comprising execution of the non-transitory machine readable instruction by the processor to:
determine a travel route from a current location of the client device of the user to a location of the new activity based on location information associated with the client device of the user;
update the graphical user interface of the client device of the user with the travel route information and a departure time based on a time of the new activity in the calendar of the user;
determine a travel route from a current location of the client device of the at least one other user to a location of the new activity based on location information associated with the client device of the at least one other user; and
update a graphical user interface of the client device of the at least one other user with the travel route information and a departure time based on a time of the new activity in the calendar of the at least one other user.

16. The computer implemented method according to claim 1, the method further comprising:
automatically purchasing a service from the third party service based on the travel-related recommendation, wherein the purchased service comprises the new activity.

17. A system for generating a recommendation on a device of a user of a life management system comprising:
means for receiving data relating to the user, the data comprising biotelemetry data received from a biotelemetry device configured to be worn by the user and collect one or more of the biotelemetry data and activity data via a wireless connection between the biotelemetry device and the life management system, the activity data collected about the user and social data of the user, the social data comprising calendar entries on a calendar for the user;
automatically change a graphical user interface of a display of the user device to represent a detected mood of the user based on the collected biotelemtry data and the activity data by changing at least one of a color scheme of the display or change the graphical user interface to include different types of information associated with the detected mood;
means for accessing the calendar on a client device of the user and a calendar on a client device of at least one other user by remotely connecting to the client device of the user and the client device of the at least one other user, wherein the at least one other user is identified as a contact by the life management system in a corresponding contact application of the client device of the user;
means for analyzing the calendar on the client device of the user and the calendar on the client device of the at least one other user;
means for identifying an open time slot in the calendar of the user that is common to an open time slot identified by the life management system in the calendar of the at least one other user;
means for generating an entry in the open time slot in the calendar of the user reserving the open time slot for a new activity and generating an entry in the open time slot in the calendar of the at least one other user reserving the open time slot for the new activity
means for generating snapshot information using the biotelemetry data, and the activity data, and user profile information associated with the user;
means for determining a momentum score for the user using portions of the snapshot information;
means for comparing the momentum score to a threshold value, and determining a requirement for a new activity based on the comparison;
means for developing a travel-related recommendation to both the user and the at least one other userbased on the requirement, wherein the new activity is based on the travel-related recommendation;
means for engaging with a third party service that is configured to carry-out the new activity associated with the travel-related recommendation and
means for automatically updating the new activity in the open time slot in the calendar of the user and the open time slot in the calendar of the at least one other user with the travel-related recommendation and information related to the third-party service.

18. The system according to claim 17, wherein the system further comprises means for determining a power level of a device of the user and a device of the at least one other user; and transferring one or more of tasks and data items from the device of the user to the device of the at least one other user when the power level is below a predetermined threshold.

19. A computer-implemented method executed by a processor configured to execute non-transitory machine readable instructions, wherein execution of the non-transitory machine readable instructions by the processor causes:
receiving data from a client device worn by a user via a wireless connection, the data comprising one or more of biotelemetry data, activity data and social data collected about a user wearing the client device, the social data comprising information related to a calendar for the user;
automatically change a graphical user interface of a display of the user device to represent a detected mood of the user based on the collected biotelemtry data and the activity data by changing at least one of a color scheme of the display or change the graphical user interface to include different types of information associated with the detected mood;
access the calendar on a client device of the user and a calendar on a client device of at least one other user by remotely connecting to the client device of the user and the client device of the at least one other user, wherein the at least one other user is identified as a contact by the life management system in a corresponding contact application of the client device of the user;

analyze the calendar on the client device of the user and the calendar on the client device of the at least one other user;

identify an open time slot in the calendar of the user that is common to an open time slot identified by the life management system in the calendar of the at least one other user;

generating an entry in the open time slot in the calendar of the user reserving the open time slot for a new activity and generating an entry in the open time slot in the calendar of the at least one other user reserving the open time slot for the new activity;

generating snapshot information using the biotelemetry data and the activity data, and user profile information associated with the user;

determining a momentum score for the user using portions of the snapshot information;

comparing the momentum score to a threshold value, and determining a requirement for the new activity based on the comparison;

developing a travel-related recommendation to both the user and the at least one other user based on the requirement, wherein the new activity is based on the travel-related recommendation;

engage with a third party service that is configured to carry-out the new activity associated with the travel-related recommendation; and automatically updating the new activity in the open time slot in the calendar of the user and the open time slot in the calendar of the at least one other user with the travel-related recommendation and information related to the third-party service.

20. The computer-implemented method according to claim 19, further comprising determining a power level of a device of the user and a device of the at least one other user; and transferring one or more of tasks and data items from the device of the user to the device of the at least one other user when the power level is below a predetermined threshold.

* * * * *